(12) United States Patent
Kossmann et al.

(10) Patent No.: US 6,815,581 B2
(45) Date of Patent: Nov. 9, 2004

(54) PLANTS WHICH SYNTHESIZE A MODIFIED STARCH, PROCESS FOR THE PRODUCTION THEREOF AND MODIFIED STARCH

(75) Inventors: Jens Kossmann, Golm (DE); Ruth Lorberth, Berlin (DE)

(73) Assignee: PlantTec Biotechnologies, GmbH (DE)

( * ) Notice: Subject to any disclaimer, the term of this patent is extended or adjusted under 35 U.S.C. 154(b) by 173 days.

(21) Appl. No.: 09/746,390

(22) Filed: Dec. 21, 2000

(65) Prior Publication Data

US 2001/0007155 A1 Jul. 5, 2001

Related U.S. Application Data

(62) Division of application No. 09/045,360, filed on Mar. 19, 1998, now Pat. No. 6,207,880, which is a continuation of application No. PCT/EP96/04109, filed on Sep. 19, 1996.

(30) Foreign Application Priority Data

Sep. 19, 1995 (DE) .......................................... 195 34 759
Dec. 20, 1995 (DE) .......................................... 195 47 733

(51) Int. Cl.[7] .................... C12N 15/29; C12N 15/82; C12P 19/04; A01H 5/00; A01H 5/06
(52) U.S. Cl. .................... 800/284; 800/278; 800/286; 800/317.2; 800/320; 800/320.1; 800/320.2; 800/320.3; 435/320.1; 435/419; 536/23.6; 536/24.5
(58) Field of Search .................... 800/278, 284, 800/283, 317.2, 320, 320.1, 320.2, 320.3, 285, 286; 435/320.1, 419, 417, 429, 101; 536/23.6, 24.5

(56) References Cited

U.S. PATENT DOCUMENTS

| 5,349,123 A | 9/1994 | Shewmaker et al. ........ 800/205 |
| 6,013,861 A | * 1/2000 | Bird et al. ................... 800/284 |

FOREIGN PATENT DOCUMENTS

| AU | B-19028/95 | 10/1995 |
| EP | 368 506 | 5/1990 |
| WO | WO 92/11375 | 7/1992 |
| WO | WO 94/09144 | 4/1994 |
| WO | WO 95/07355 | 3/1995 |
| WO | WO 95/26407 | 10/1995 |

OTHER PUBLICATIONS

Ritte et al. Proc. Natl. Acad. Sci. USA 99(10): 7166–7171 (May 2002).*
Evans et al. Biochem. Soc. Trans. 20:344S, 1992.*
Mazzolini et al. Plant Mol. Biol. 20:715–731, 1992.*
Kull et al. J. Genet. Breed. 49(1):69–76, 1995.*
Konecki et al., "The Primary Strucutre of Human Chromogranin A and Pancreastatin," *J. Biol. Chem.*, 262(35), pp. 17026–17030 (1987).
Kossmann et al., "Carbohydrate Bioengineering," *Progress Biotechnol.*, 10, pp. 271–278 (1995).
Napoli et al., "Introduction of a Chimeric Chalcone Synthase Gene into Petunia Resluts in Reversible Co–Suppression of Homologous Genes *in trans*," *Plant Cell*, 2, pp. 279–289 (1990).
Newman et al., "Genes Galore: a Summary of Methods for Accessing Results from Large–scale Partial Sequencing of Anonymous Arabidopsis cDNA Clones," *Plant Physiol.*, 106, pp. 1241–1255 (1994).
Sonnewald et al., "A Second L–Type Isozyme of Potato Glucan Phosphorylase: Cloning, Antisense Inhibition and Expression Analysis," *Plant Molec. Biol.*, 27(3), pp. 567–576 (1995).
St. –Pierre et al., "The Starch Phosphorylase Gene is Subjected to Different Modes of Regulation in Starch–containing Tissues of Potato," *Plant Molec. Biol.*, 30(6), pp. 1087–1098 (1996).

* cited by examiner

*Primary Examiner*—David T. Fox
(74) *Attorney, Agent, or Firm*—Fish & Neave; James F. Haley, Jr.; Grant Kalinowski

(57) ABSTRACT

Nucleic acid molecules are described encoding a starch granule-bound protein as well as methods and recombinant DNA molecules for the production of transgenic plant cells and plants synthesizing a modified starch with modified viscosity properties and a modified phosphate content. Moreover, the plant cells and plants resulting from those methods as well as the starch obtainable therefrom are described.

36 Claims, 4 Drawing Sheets

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
         (A) LENGTH: 4856 base pairs
         (B) TYPE: nucleotide
         (C) STRANDEDNESS: single
         (D) TOPOLOGY: linear (ii) MOLECULE TYPE: cDNA to mRNA (vi) ORIGINAL SOURCE:
         (A) ORGANISM: Solanum tuberosum
         (B) STRAIN: C.V. Berolina (ix) FEATURE:
         (A) NAME/KEY: CDS
         (B) LOCATION:105..4497

(xi) SEQUENCE DESCRIPTION: SEQ ID NO: 1:

```
CATCTTCATC GAATTTCTCG AAGCTTCTTC GCTAATTTCC TGGTTTCTTC ACTCAAAATC          60

GACGTTTCTA GCTGAACTTG AGTGAATTAA GCCAGTGGGA GGAT ATG AGT AAT TCC         116
                                                Met Ser Asn Ser
                                                  1

TTA GGG AAT AAC TTG CTG TAC CAG GGA TTC CTA ACC TCA ACA GTG TTG          164
Leu Gly Asn Asn Leu Leu Tyr Gln Gly Phe Leu Thr Ser Thr Val Leu
  5                  10                  15                  20

GAA CAT AAA AGT AGA ATC AGT CCT CCT TGT GTT GGA GGC AAT TCT TTG          212
Glu His Lys Ser Arg Ile Ser Pro Pro Cys Val Gly Gly Asn Ser Leu
                 25                  30                  35

TTT CAA CAA CAA GTG ATC TCG AAA TCA CCT TTA TCA ACT GAG TTT CGA          260
Phe Gln Gln Gln Val Ile Ser Lys Ser Pro Leu Ser Thr Glu Phe Arg
             40                  45                  50

GGT AAC AGG TTA AAG GTG CAG AAA AAG AAA ATA CCT ATG GAA AAG AAG          308
Gly Asn Arg Leu Lys Val Gln Lys Lys Lys Ile Pro Met Glu Lys Lys
         55                  60                  65

CGT GCT TTT TCT AGT TCT CCT CAT GCT GTA CTT ACC ACT GAT ACC TCT          356
Arg Ala Phe Ser Ser Ser Pro His Ala Val Leu Thr Thr Asp Thr Ser
     70                  75                  80

TCT GAG CTA GCA GAA AAG TTC AGT CTA GGG GGG AAT ATT GAG CTA CAG          404
Ser Glu Leu Ala Glu Lys Phe Ser Leu Gly Gly Asn Ile Glu Leu Gln
 85                  90                  95                 100

GTT GAT GTT AGG CCT CCC ACT TCA GGT GAT GTG TCC TTT GTG GAT TTT          452
Val Asp Val Arg Pro Pro Thr Ser Gly Asp Val Ser Phe Val Asp Phe
                105                 110                 115

CAA GTA ACA AAT GGT AGT GAT AAA CTG TTT TTG CAC TGG GGG GCA GTA          500
Gln Val Thr Asn Gly Ser Asp Lys Leu Phe Leu His Trp Gly Ala Val
            120                 125                 130

AAA TTC GGG AAA GAA ACA TGG TCT CTT CCG AAT GAT CGT CCA GAT GGG          548
Lys Phe Gly Lys Glu Thr Trp Ser Leu Pro Asn Asp Arg Pro Asp Gly
        135                 140                 145

ACC AAA GTG TAC AAG AAC AAA GCA CTT AGA ACT CCA TTT GTT AAA TCT          596
Thr Lys Val Tyr Lys Asn Lys Ala Leu Arg Thr Pro Phe Val Lys Ser
    150                 155                 160

GGC TCT AAC TCC ATC CTG AGA CTG GAG ATA CGA GAC ACT GCT ATC GAA          644
Gly Ser Asn Ser Ile Leu Arg Leu Glu Ile Arg Asp Thr Ala Ile Glu
165                 170                 175                 180

GCT ATT GAG TTT CTC ATA TAC GAT GAA GCC CAC GAT AAA TGG ATA AAG          692
```

```
Ala Ile Glu Phe Leu Ile Tyr Asp Glu Ala His Asp Lys Trp Ile Lys
            185                 190                 195

AAT AAT GGT GGT AAT TTT CGT GTC AAA TTG TCA AGA AAA GAG ATA CGA     740
Asn Asn Gly Gly Asn Phe Arg Val Lys Leu Ser Arg Lys Glu Ile Arg
            200                 205                 210

GGC CCA GAT GTT TCT GTT CCT GAG GAG CTT GTA CAG ATC CAA TCA TAT     788
Gly Pro Asp Val Ser Val Pro Glu Glu Leu Val Gln Ile Gln Ser Tyr
            215                 220                 225

TTG AGG TGG GAG AGG AAG GGA AAA CAG AAT TAC CCC CCT GAG AAA GAG     836
Leu Arg Trp Glu Arg Lys Gly Lys Gln Asn Tyr Pro Pro Glu Lys Glu
        230                 235                 240

AAG GAG GAA TAT GAG GCT GCT CGA ACT GTG CTA CAG GAG GAA ATA GCT     884
Lys Glu Glu Tyr Glu Ala Ala Arg Thr Val Leu Gln Glu Glu Ile Ala
245                 250                 255                 260

CGT GGT GCT TCC ATA CAG GAC ATT CGA GCA AGG CTA ACA AAA ACT AAT     932
Arg Gly Ala Ser Ile Gln Asp Ile Arg Ala Arg Leu Thr Lys Thr Asn
                265                 270                 275

GAT AAA AGT CAA AGC AAA GAA GAG CCT CTT CAT GTA ACA AAG AGT GAT     980
Asp Lys Ser Gln Ser Lys Glu Glu Pro Leu His Val Thr Lys Ser Asp
                280                 285                 290

ATA CCT GAT GAC CTT GCC CAA GCA CAA GCT TAC ATT AGG TGG GAG AAA    1028
Ile Pro Asp Asp Leu Ala Gln Ala Gln Ala Tyr Ile Arg Trp Glu Lys
            295                 300                 305

GCA GGA AAG CCG AAC TAT CCT CCA GAA AAG CAA ATT GAA GAA CTC GAA    1076
Ala Gly Lys Pro Asn Tyr Pro Pro Glu Lys Gln Ile Glu Glu Leu Glu
        310                 315                 320

GAA GCA AGA AGA GAA TTG CAA CTT GAG CTT GAG AAA GGC ATT ACC CTT    1124
Glu Ala Arg Arg Glu Leu Gln Leu Glu Leu Glu Lys Gly Ile Thr Leu
325                 330                 335                 340

GAT GAG TTG CGG AAA ACG ATT ACA AAA GGG GAG ATA AAA ACT AAG GTG    1172
Asp Glu Leu Arg Lys Thr Ile Thr Lys Gly Glu Ile Lys Thr Lys Val
                345                 350                 355

GAA AAG CAC CTG AAA AGA AGT TCT TTT GCC GTT GAA AGA ATC CAA AGA    1220
Glu Lys His Leu Lys Arg Ser Ser Phe Ala Val Glu Arg Ile Gln Arg
                360                 365                 370

AAG AAG AGA GAC TTT GGG CAT CTT ATT AAT AAG TAT ACT TCC AGT CCT    1268
Lys Lys Arg Asp Phe Gly His Leu Ile Asn Lys Tyr Thr Ser Ser Pro
            375                 380                 385

GCA GTA CAA GTA CAA AAG GTC TTG GAA GAA CCA CCA GCC TTA TCT AAA    1316
Ala Val Gln Val Gln Lys Val Leu Glu Glu Pro Pro Ala Leu Ser Lys
        390                 395                 400

ATT AAG CTG TAT GCC AAG GAG AAG GAG GAG CAG ATT GAT GAT CCG ATC    1364
Ile Lys Leu Tyr Ala Lys Glu Lys Glu Glu Gln Ile Asp Asp Pro Ile
405                 410                 415                 420

CTA AAT AAA AAG ATC TTT AAG GTC GAT GAT GGG GAG CTA CTG GTA CTG    1412
Leu Asn Lys Lys Ile Phe Lys Val Asp Asp Gly Glu Leu Leu Val Leu
                425                 430                 435

GTA GCA AAG TCC TCT GGG AAG ACA AAA GTA CAT CTA GCT ACA GAT CTG    1460
Val Ala Lys Ser Ser Gly Lys Thr Lys Val His Leu Ala Thr Asp Leu
                440                 445                 450

AAT CAG CCA ATT ACT CTT CAC TGG GCA TTA TCC AAA AGT CCT GGA GAG    1508
Asn Gln Pro Ile Thr Leu His Trp Ala Leu Ser Lys Ser Pro Gly Glu
            455                 460                 465

TGG ATG GTA CCA CCT TCA AGC ATA TTG CCT CCT GGG TCA ATT ATT TTA    1556
Trp Met Val Pro Pro Ser Ser Ile Leu Pro Pro Gly Ser Ile Ile Leu
        470                 475                 480

GAC AAG GCT GCC GAA ACA CCT TTT TCA GCC AGT TCT TCT GAT GGT CTA    1604
Asp Lys Ala Ala Glu Thr Pro Phe Ser Ala Ser Ser Ser Asp Gly Leu
485                 490                 495                 500
```

-continued

| | |
|---|---|
| ACT TCT AAG GTA CAA TCT TTG GAT ATA GTA ATT GAA GAT GGC AAT TTT<br>Thr Ser Lys Val Gln Ser Leu Asp Ile Val Ile Glu Asp Gly Asn Phe<br>                      505                          510                          515 | 1652 |
| GTG GGG ATG CCA TTT GTT CTT TTG TCT GGT GAA AAA TGG ATT AAG AAC<br>Val Gly Met Pro Phe Val Leu Leu Ser Gly Glu Lys Trp Ile Lys Asn<br>                  520                          525                          530 | 1700 |
| CAA GGG TCG GAT TTC TAT GTT GGC TTC AGT GCT GCA TCC AAA TTA GCA<br>Gln Gly Ser Asp Phe Tyr Val Gly Phe Ser Ala Ala Ser Lys Leu Ala<br>                  535                          540                          545 | 1748 |
| CTC AAG GCT GCT GGG GAT GGC AGT GGA ACT GCA AAG TCT TTA CTG GAT<br>Leu Lys Ala Ala Gly Asp Gly Ser Gly Thr Ala Lys Ser Leu Leu Asp<br>550                          555                          560 | 1796 |
| AAA ATA GCA GAT ATG GAA AGT GAG GCT CAG AAG TCA TTT ATG CAC CGG<br>Lys Ile Ala Asp Met Glu Ser Glu Ala Gln Lys Ser Phe Met His Arg<br>565                          570                          575                          580 | 1844 |
| TTT AAT ATT GCA GCT GAC TTG ATA GAA GAT GCC ACT AGT GCT GGT GAA<br>Phe Asn Ile Ala Ala Asp Leu Ile Glu Asp Ala Thr Ser Ala Gly Glu<br>                  585                          590                          595 | 1892 |
| CTT GGT TTT GCT GGA ATT CTT GTA TGG ATG AGG TTC ATG GCT ACA AGG<br>Leu Gly Phe Ala Gly Ile Leu Val Trp Met Arg Phe Met Ala Thr Arg<br>                  600                          605                          610 | 1940 |
| CAA CTG ATA TGG AAC AAA AAC TAT AAC GTA AAA CCA CGT GAA ATA AGC<br>Gln Leu Ile Trp Asn Lys Asn Tyr Asn Val Lys Pro Arg Glu Ile Ser<br>                  615                          620                          625 | 1988 |
| AAG GCT CAG GAC AGA CTT ACA GAC TTG TTG CAG AAT GCT TTC ACC AGT<br>Lys Ala Gln Asp Arg Leu Thr Asp Leu Leu Gln Asn Ala Phe Thr Ser<br>630                          635                          640 | 2036 |
| CAC CCT CAG TAC CGT GAA ATT TTG CGG ATG ATT ATG TCA ACT GTT GGA<br>His Pro Gln Tyr Arg Glu Ile Leu Arg Met Ile Met Ser Thr Val Gly<br>645                          650                          655                          660 | 2084 |
| CGT GGA GGT GAA GGG GAT GTA GGA CAG CGA ATT AGG GAT GAA ATT TTG<br>Arg Gly Gly Glu Gly Asp Val Gly Gln Arg Ile Arg Asp Glu Ile Leu<br>                  665                          670                          675 | 2132 |
| GTC ATC CAG AGG AAC AAT GAC TGC AAG GGT GGT ATG ATG CAA GAA TGG<br>Val Ile Gln Arg Asn Asn Asp Cys Lys Gly Gly Met Met Gln Glu Trp<br>                  680                          685                          690 | 2180 |
| CAT CAG AAA TTG CAT AAT AAT ACT AGT CCT GAT GAT GTT GTG ATC TGT<br>His Gln Lys Leu His Asn Asn Thr Ser Pro Asp Asp Val Val Ile Cys<br>                  695                          700                          705 | 2228 |
| CAG GCA TTA ATT GAC TAC ATC AAG AGT GAT TTT GAT CTT GGT GTT TAT<br>Gln Ala Leu Ile Asp Tyr Ile Lys Ser Asp Phe Asp Leu Gly Val Tyr<br>710                          715                          720 | 2276 |
| TGG AAA ACC CTG AAT GAG AAC GGA ATA ACA AAA GAG CGT CTT TTG AGT<br>Trp Lys Thr Leu Asn Glu Asn Gly Ile Thr Lys Glu Arg Leu Leu Ser<br>725                          730                          735                          740 | 2324 |
| TAT GAC CGT GCT ATC CAT TCT GAA CCA AAT TTT AGA GGA GAT CAA AAG<br>Tyr Asp Arg Ala Ile His Ser Glu Pro Asn Phe Arg Gly Asp Gln Lys<br>                  745                          750                          755 | 2372 |
| GGT GGT CTT TTG CGT GAT TTA GGT CAC TAT ATG AGA ACA TTG AAG GCA<br>Gly Gly Leu Leu Arg Asp Leu Gly His Tyr Met Arg Thr Leu Lys Ala<br>                  760                          765                          770 | 2420 |
| GTT CAT TCA GGT GCA GAT CTT GAG TCT GCT ATT GCA AAC TGC ATG GGC<br>Val His Ser Gly Ala Asp Leu Glu Ser Ala Ile Ala Asn Cys Met Gly<br>                  775                          780                          785 | 2468 |
| TAC AAA ACT GAG GGA GAA GGC TTT ATG GTT GGA GTC CAG ATA AAT CCT<br>Tyr Lys Thr Glu Gly Glu Gly Phe Met Val Gly Val Gln Ile Asn Pro<br>                  790                          795                          800 | 2516 |
| GTA TCA GGC TTG CCA TCT GGC TTT CAG GAC CTC CTC CAT TTT GTC TTA<br>Val Ser Gly Leu Pro Ser Gly Phe Gln Asp Leu Leu His Phe Val Leu<br>805                          810                          815                          820 | 2564 |

-continued

```
GAC CAT GTG GAA GAT AAA AAT GTG GAA ACT CTT CTT GAG AGA TTG CTA      2612
Asp His Val Glu Asp Lys Asn Val Glu Thr Leu Leu Glu Arg Leu Leu
            825                 830                 835

GAG GCT CGT GAG GAG CTT AGG CCC TTG CTT CTC AAA CCA AAC AAC CGT      2660
Glu Ala Arg Glu Glu Leu Arg Pro Leu Leu Leu Lys Pro Asn Asn Arg
            840                 845                 850

CTA AAG GAT CTG CTG TTT TTG GAC ATA GCA CTT GAT TCT ACA GTT AGA      2708
Leu Lys Asp Leu Leu Phe Leu Asp Ile Ala Leu Asp Ser Thr Val Arg
            855                 860                 865

ACA GCA GTA GAA AGG GGA TAT GAA GAA TTG AAC AAC GCT AAT CCT GAG      2756
Thr Ala Val Glu Arg Gly Tyr Glu Glu Leu Asn Asn Ala Asn Pro Glu
        870                 875                 880

AAA ATC ATG TAC TTC ATC TCC CTC GTT CTT GAA AAT CTC GCA CTC TCT      2804
Lys Ile Met Tyr Phe Ile Ser Leu Val Leu Glu Asn Leu Ala Leu Ser
885                 890                 895                 900

GTG GAC GAT AAT GAA GAT CTT GTT TAT TGC TTG AAG GGA TGG AAT CAA      2852
Val Asp Asp Asn Glu Asp Leu Val Tyr Cys Leu Lys Gly Trp Asn Gln
            905                 910                 915

GCT CTT TCA ATG TCC AAT GGT GGG GAC AAC CAT TGG GCT TTA TTT GCA      2900
Ala Leu Ser Met Ser Asn Gly Gly Asp Asn His Trp Ala Leu Phe Ala
            920                 925                 930

AAA GCT GTG CTT GAC AGA ACC CGT CTT GCA CTT GCA AGC AAG GCA GAG      2948
Lys Ala Val Leu Asp Arg Thr Arg Leu Ala Leu Ala Ser Lys Ala Glu
            935                 940                 945

TGG TAC CAT CAC TTA TTG CAG CCA TCT GCC GAA TAT CTA GGA TCA ATA      2996
Trp Tyr His His Leu Leu Gln Pro Ser Ala Glu Tyr Leu Gly Ser Ile
        950                 955                 960

CTT GGG GTG GAC CAA TGG GCT TTG AAC ATA TTT ACT GAA GAA ATT ATA      3044
Leu Gly Val Asp Gln Trp Ala Leu Asn Ile Phe Thr Glu Glu Ile Ile
965                 970                 975                 980

CGT GCT GGA TCA GCA GCT TCA TTA TCC TCT CTT CTT AAT AGA CTC GAT      3092
Arg Ala Gly Ser Ala Ala Ser Leu Ser Ser Leu Leu Asn Arg Leu Asp
            985                 990                 995

CCC GTG CTT CGG AAA ACT GCA AAT CTA GGA AGT TGG CAG ATT ATC AGT      3140
Pro Val Leu Arg Lys Thr Ala Asn Leu Gly Ser Trp Gln Ile Ile Ser
            1000                1005                1010

CCA GTT GAA GCC GTT GGA TAT GTT GTC GTT GTG GAT GAG TTG CTT TCA      3188
Pro Val Glu Ala Val Gly Tyr Val Val Val Val Asp Glu Leu Leu Ser
            1015                1020                1025

GTT CAG AAT GAA ATC TAC GAG AAG CCC ACG ATC TTA GTA GCA AAA TCT      3236
Val Gln Asn Glu Ile Tyr Glu Lys Pro Thr Ile Leu Val Ala Lys Ser
            1030                1035                1040

GTT AAA GGA GAG GAG GAA ATT CCT GAT GGT GCT GTT GCC CTG ATA ACA      3284
Val Lys Gly Glu Glu Glu Ile Pro Asp Gly Ala Val Ala Leu Ile Thr
1045                1050                1055                1060

CCA GAC ATG CCA GAT GTT CTT TCA CAT GTT TCT GTT CGA GCT AGA AAT      3332
Pro Asp Met Pro Asp Val Leu Ser His Val Ser Val Arg Ala Arg Asn
            1065                1070                1075

GGG AAG GTT TGC TTT GCT ACA TGC TTT GAT CCC AAT ATA TTG GCT GAC      3380
Gly Lys Val Cys Phe Ala Thr Cys Phe Asp Pro Asn Ile Leu Ala Asp
            1080                1085                1090

CTC CAA GCA AAG GAA GGA AGG ATT TTG CTC TTA AAG CCT ACA CCT TCA      3428
Leu Gln Ala Lys Glu Gly Arg Ile Leu Leu Leu Lys Pro Thr Pro Ser
            1095                1100                1105

GAC ATA ATC TAT AGT GAG GTG AAT GAG ATT GAG CTC CAA AGT TCA AGT      3476
Asp Ile Ile Tyr Ser Glu Val Asn Glu Ile Glu Leu Gln Ser Ser Ser
        1110                1115                1120

AAC TTG GTA GAA GCT GAA ACT TCA GCA ACA CTT AGA TTG GTG AAA AAG      3524
Asn Leu Val Glu Ala Glu Thr Ser Ala Thr Leu Arg Leu Val Lys Lys
```

-continued

```
                1125                1130                1135                1140
CAA TTT GGT GGT TGT TAC GCA ATA TCA GCA GAT GAA TTC ACA AGT GAA           3572
Gln Phe Gly Gly Cys Tyr Ala Ile Ser Ala Asp Glu Phe Thr Ser Glu
                      1145                1150                1155

ATG GTT GGA GCT AAA TCA CGT AAT ATT GCA TAT CTG AAA GGA AAA GTG           3620
Met Val Gly Ala Lys Ser Arg Asn Ile Ala Tyr Leu Lys Gly Lys Val
                1160                1165                1170

CCT TCC TCG GTG GGA ATT CCT ACG TCA GTA GCT CTT CCA TTT GGA GTC           3668
Pro Ser Ser Val Gly Ile Pro Thr Ser Val Ala Leu Pro Phe Gly Val
            1175                1180                1185

TTT GAG AAA GTA CTT TCA GAC GAC ATA AAT CAG GGA GTG GCA AAA GAG           3716
Phe Glu Lys Val Leu Ser Asp Asp Ile Asn Gln Gly Val Ala Lys Glu
        1190                1195                1200

TTG CAA ATT CTG ATG AAA AAA CTA TCT GAA GGA GAC TTC AGC GCT CTT           3764
Leu Gln Ile Leu Met Lys Lys Leu Ser Glu Gly Asp Phe Ser Ala Leu
1205                1210                1215                1220

GGT GAA ATT CGC ACA ACG GTT TTA GAT CTT TCA GCA CCA GCT CAA TTG           3812
Gly Glu Ile Arg Thr Thr Val Leu Asp Leu Ser Ala Pro Ala Gln Leu
                    1225                1230                1235

GTC AAA GAG CTG AAG GAG AAG ATG CAG GGT TCT GGC ATG CCT TGG CCT           3860
Val Lys Glu Leu Lys Glu Lys Met Gln Gly Ser Gly Met Pro Trp Pro
                1240                1245                1250

GGT GAT GAA GGT CCA AAG CGG TGG GAA CAA GCA TGG ATG GCC ATA AAA           3908
Gly Asp Glu Gly Pro Lys Arg Trp Glu Gln Ala Trp Met Ala Ile Lys
            1255                1260                1265

AAG GTG TGG GCT TCA AAA TGG AAT GAG AGA GCA TAC TTC AGC ACA AGG           3956
Lys Val Trp Ala Ser Lys Trp Asn Glu Arg Ala Tyr Phe Ser Thr Arg
        1270                1275                1280

AAG GTG AAA CTG GAT CAT GAC TAT CTG TGC ATG GCT GTC CTT GTT CAA           4004
Lys Val Lys Leu Asp His Asp Tyr Leu Cys Met Ala Val Leu Val Gln
1285                1290                1295                1300

GAA ATA ATA AAT GCT GAT TAT GCA TTT GTC ATT CAC ACA ACC AAC CCA           4052
Glu Ile Ile Asn Ala Asp Tyr Ala Phe Val Ile His Thr Thr Asn Pro
                    1305                1310                1315

TCT TCC GGA GAC GAC TCA GAA ATA TAT GCC GAG GTG GTC AGG GGC CTT           4100
Ser Ser Gly Asp Asp Ser Glu Ile Tyr Ala Glu Val Val Arg Gly Leu
                1320                1325                1330

GGG GAA ACA CTT GTT GGA GCT TAT CCA GGA CGT GCT TTG AGT TTT ATC           4148
Gly Glu Thr Leu Val Gly Ala Tyr Pro Gly Arg Ala Leu Ser Phe Ile
            1335                1340                1345

TGC AAG AAA AAG GAT CTC AAC TCT CCT CAA GTG TTA GGT TAC CCA AGC           4196
Cys Lys Lys Lys Asp Leu Asn Ser Pro Gln Val Leu Gly Tyr Pro Ser
        1350                1355                1360

AAA CCG ATC GGC CTT TTC ATA AAA AGA TCT ATC ATC TTC CGA TCT GAT           4244
Lys Pro Ile Gly Leu Phe Ile Lys Arg Ser Ile Ile Phe Arg Ser Asp
1365                1370                1375                1380

TCC AAT GGG GAA GAT TTG GAA GGT TAT GCC GGT GCT GGC CTC TAC GAC           4292
Ser Asn Gly Glu Asp Leu Glu Gly Tyr Ala Gly Ala Gly Leu Tyr Asp
                    1385                1390                1395

AGT GTA CCA ATG GAT GAG GAG GAA AAA GTT GTA ATT GAT TAC TCT TCC           4340
Ser Val Pro Met Asp Glu Glu Glu Lys Val Val Ile Asp Tyr Ser Ser
                1400                1405                1410

GAC CCA TTG ATA ACT GAT GGT AAC TTC CGC CAG ACA ATC CTG TCC AAC           4388
Asp Pro Leu Ile Thr Asp Gly Asn Phe Arg Gln Thr Ile Leu Ser Asn
            1415                1420                1425

ATT GCT CGT GCT GGA CAT GCT ATC GAG GAG CTA TAT GGC TCT CCT CAA           4436
Ile Ala Arg Ala Gly His Ala Ile Glu Glu Leu Tyr Gly Ser Pro Gln
        1430                1435                1440

GAC ATT GAG GGT GTA GTG AGG GAT GGA AAG ATT TAT GTC GTT CAG ACA           4484
```

-continued

```
Asp Ile Glu Gly Val Val Arg Asp Gly Lys Ile Tyr Val Val Gln Thr
1445                1450                1455                1460

AGA CCA CAG ATG T GATTATATTC TCGTTGTATG TTGTTCAGAG AAGACCACAG      4537
Arg Pro Gln Met

ATGTGATCAT ATTCTCATTG TATCAGATCT GTGACCACTT ACCTGATACC TCCCATGAAG   4597

TTACCTGTAT GATTATACGT GATCCAAAGC CATCACATCA TGTTCACCTT CAGCTATTGG   4657

AGGAGAAGTG AGAAGTAGGA ATTGCAATAT GAGGAATAAT AAGAAAAACT TTGTAAAAGC   4717

TAAATTAGCT GGGTATGATA TAGGGAGAAA TGTGTAAACA TTGTACTATA TATAGTATAT   4777

ACACACGCAT TATGTATTGC ATTATGCACT GAATAATATC GCAGCATCAA AGAAGAAATC   4837

CTTTGGGTGG TTTCAAAAA                                                4856
```

(2) INFORMATION FOR SEQ ID NO: 2:

(i) SEQUENCE CHARACTERISTICS:
        (A) LENGTH: 1464 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Val Ile Ser Lys Ser Pro Leu Ser
        35                  40                  45

Thr Glu Phe Arg Gly Asn Arg Leu Lys Val Gln Lys Lys Lys Ile Pro
    50                  55                  60

Met Glu Lys Lys Arg Ala Phe Ser Ser Pro His Ala Val Leu Thr
65                  70                  75                  80

Thr Asp Thr Ser Ser Glu Leu Ala Glu Lys Phe Ser Leu Gly Gly Asn
            85                  90                  95

Ile Glu Leu Gln Val Asp Val Arg Pro Pro Thr Ser Gly Asp Val Ser
            100                 105                 110

Phe Val Asp Phe Gln Val Thr Asn Gly Ser Asp Lys Leu Phe Leu His
            115                 120                 125

Trp Gly Ala Val Lys Phe Gly Lys Glu Thr Trp Ser Leu Pro Asn Asp
130                 135                 140

Arg Pro Asp Gly Thr Lys Val Tyr Lys Asn Lys Ala Leu Arg Thr Pro
145                 150                 155                 160

Phe Val Lys Ser Gly Ser Asn Ser Ile Leu Arg Leu Glu Ile Arg Asp
            165                 170                 175

Thr Ala Ile Glu Ala Ile Glu Phe Leu Ile Tyr Asp Glu Ala His Asp
            180                 185                 190

Lys Trp Ile Lys Asn Asn Gly Gly Asn Phe Arg Val Lys Leu Ser Arg
            195                 200                 205

Lys Glu Ile Arg Gly Pro Asp Val Ser Val Pro Glu Leu Val Gln
    210                 215                 220

Ile Gln Ser Tyr Leu Arg Trp Glu Arg Lys Gly Lys Gln Asn Tyr Pro
225                 230                 235                 240

Pro Glu Lys Glu Lys Glu Glu Tyr Glu Ala Ala Arg Thr Val Leu Gln
            245                 250                 255

Glu Glu Ile Ala Arg Gly Ala Ser Ile Gln Asp Ile Arg Ala Arg Leu
```

-continued

```
                260                 265                 270
Thr Lys Thr Asn Asp Lys Ser Gln Ser Lys Glu Glu Pro Leu His Val
            275                 280                 285
Thr Lys Ser Asp Ile Pro Asp Asp Leu Ala Gln Ala Gln Ala Tyr Ile
            290                 295                 300
Arg Trp Glu Lys Ala Gly Lys Pro Asn Tyr Pro Pro Glu Lys Gln Ile
305                 310                 315                 320
Glu Glu Leu Glu Glu Ala Arg Arg Glu Leu Gln Leu Glu Leu Glu Lys
            325                 330                 335
Gly Ile Thr Leu Asp Glu Leu Arg Lys Thr Ile Thr Lys Gly Glu Ile
            340                 345                 350
Lys Thr Lys Val Glu Lys His Leu Lys Arg Ser Ser Phe Ala Val Glu
            355                 360                 365
Arg Ile Gln Arg Lys Lys Arg Asp Phe Gly His Leu Ile Asn Lys Tyr
            370                 375                 380
Thr Ser Ser Pro Ala Val Gln Val Gln Lys Val Leu Glu Glu Pro Pro
385                 390                 395                 400
Ala Leu Ser Lys Ile Lys Leu Tyr Ala Lys Glu Lys Glu Glu Gln Ile
            405                 410                 415
Asp Asp Pro Ile Leu Asn Lys Lys Ile Phe Lys Val Asp Asp Gly Glu
            420                 425                 430
Leu Leu Val Leu Val Ala Lys Ser Ser Gly Lys Thr Lys Val His Leu
            435                 440                 445
Ala Thr Asp Leu Asn Gln Pro Ile Thr Leu His Trp Ala Leu Ser Lys
            450                 455                 460
Ser Pro Gly Glu Trp Met Val Pro Pro Ser Ile Leu Pro Pro Gly
465                 470                 475                 480
Ser Ile Ile Leu Asp Lys Ala Ala Glu Thr Pro Phe Ser Ala Ser Ser
            485                 490                 495
Ser Asp Gly Leu Thr Ser Lys Val Gln Ser Leu Asp Ile Val Ile Glu
            500                 505                 510
Asp Gly Asn Phe Val Gly Met Pro Phe Val Leu Leu Ser Gly Glu Lys
            515                 520                 525
Trp Ile Lys Asn Gln Gly Ser Asp Phe Tyr Val Gly Phe Ser Ala Ala
530                 535                 540
Ser Lys Leu Ala Leu Lys Ala Ala Gly Asp Gly Ser Gly Thr Ala Lys
545                 550                 555                 560
Ser Leu Leu Asp Lys Ile Ala Asp Met Glu Ser Glu Ala Gln Lys Ser
            565                 570                 575
Phe Met His Arg Phe Asn Ile Ala Ala Asp Leu Ile Glu Asp Ala Thr
            580                 585                 590
Ser Ala Gly Glu Leu Gly Phe Ala Gly Ile Leu Val Trp Met Arg Phe
            595                 600                 605
Met Ala Thr Arg Gln Leu Ile Trp Asn Lys Asn Tyr Asn Val Lys Pro
            610                 615                 620
Arg Glu Ile Ser Lys Ala Gln Asp Arg Leu Thr Asp Leu Leu Gln Asn
625                 630                 635                 640
Ala Phe Thr Ser His Pro Gln Tyr Arg Glu Ile Leu Arg Met Ile Met
            645                 650                 655
Ser Thr Val Gly Arg Gly Gly Glu Gly Asp Val Gly Gln Arg Ile Arg
            660                 665                 670
Asp Glu Ile Leu Val Ile Gln Arg Asn Asn Asp Cys Lys Gly Gly Met
            675                 680                 685
```

```
Met Gln Glu Trp His Gln Lys Leu His Asn Asn Thr Ser Pro Asp Asp
    690                 695                 700
Val Val Ile Cys Gln Ala Leu Ile Asp Tyr Ile Lys Ser Asp Phe Asp
705                 710                 715                 720
Leu Gly Val Tyr Trp Lys Thr Leu Asn Glu Asn Gly Ile Thr Lys Glu
                725                 730                 735
Arg Leu Leu Ser Tyr Asp Arg Ala Ile His Ser Glu Pro Asn Phe Arg
            740                 745                 750
Gly Asp Gln Lys Gly Leu Leu Arg Asp Leu Gly His Tyr Met Arg
            755                 760                 765
Thr Leu Lys Ala Val His Ser Gly Ala Asp Leu Glu Ser Ala Ile Ala
    770                 775                 780
Asn Cys Met Gly Tyr Lys Thr Glu Gly Glu Phe Met Val Gly Val
785                 790                 795                 800
Gln Ile Asn Pro Val Ser Gly Leu Pro Ser Gly Phe Gln Asp Leu Leu
                805                 810                 815
His Phe Val Leu Asp His Val Glu Asp Lys Asn Val Glu Thr Leu Leu
            820                 825                 830
Glu Arg Leu Leu Glu Ala Arg Glu Glu Leu Arg Pro Leu Leu Leu Lys
        835                 840                 845
Pro Asn Asn Arg Leu Lys Asp Leu Leu Phe Leu Asp Ile Ala Leu Asp
    850                 855                 860
Ser Thr Val Arg Thr Ala Val Glu Arg Gly Tyr Glu Glu Leu Asn Asn
865                 870                 875                 880
Ala Asn Pro Glu Lys Ile Met Tyr Phe Ile Ser Leu Val Leu Glu Asn
                885                 890                 895
Leu Ala Leu Ser Val Asp Asp Asn Glu Asp Leu Val Tyr Cys Leu Lys
            900                 905                 910
Gly Trp Asn Gln Ala Leu Ser Met Ser Asn Gly Gly Asp Asn His Trp
        915                 920                 925
Ala Leu Phe Ala Lys Ala Val Leu Asp Arg Thr Arg Leu Ala Leu Ala
    930                 935                 940
Ser Lys Ala Glu Trp Tyr His His Leu Leu Gln Pro Ser Ala Glu Tyr
945                 950                 955                 960
Leu Gly Ser Ile Leu Gly Val Asp Gln Trp Ala Leu Asn Ile Phe Thr
                965                 970                 975
Glu Glu Ile Ile Arg Ala Gly Ser Ala Ala Ser Leu Ser Ser Leu Leu
            980                 985                 990
Asn Arg Leu Asp Pro Val Leu Arg Lys Thr Ala Asn Leu Gly Ser Trp
        995                 1000                1005
Gln Ile Ile Ser Pro Val Glu Ala Val Gly Tyr Val Val Val Val Asp
    1010                1015                1020
Glu Leu Leu Ser Val Gln Asn Glu Ile Tyr Glu Lys Pro Thr Ile Leu
1025                1030                1035                1040
Val Ala Lys Ser Val Lys Gly Glu Glu Ile Pro Asp Gly Ala Val
                1045                1050                1055
Ala Leu Ile Thr Pro Asp Met Pro Asp Val Leu Ser His Val Ser Val
            1060                1065                1070
Arg Ala Arg Asn Gly Lys Val Cys Phe Ala Thr Cys Phe Asp Pro Asn
        1075                1080                1085
Ile Leu Ala Asp Leu Gln Ala Lys Glu Gly Arg Ile Leu Leu Leu Lys
    1090                1095                1100
```

```
Pro Thr Pro Ser Asp Ile Ile Tyr Ser Glu Val Asn Glu Ile Glu Leu
1105                1110                1115                1120

Gln Ser Ser Ser Asn Leu Val Glu Ala Glu Thr Ser Ala Thr Leu Arg
            1125                1130                1135

Leu Val Lys Lys Gln Phe Gly Gly Cys Tyr Ala Ile Ser Ala Asp Glu
        1140                1145                1150

Phe Thr Ser Glu Met Val Gly Ala Lys Ser Arg Asn Ile Ala Tyr Leu
    1155                1160                1165

Lys Gly Lys Val Pro Ser Ser Val Gly Ile Pro Thr Ser Val Ala Leu
1170                1175                1180

Pro Phe Gly Val Phe Glu Lys Val Leu Ser Asp Asp Ile Asn Gln Gly
1185                1190                1195                1200

Val Ala Lys Glu Leu Gln Ile Leu Met Lys Lys Leu Ser Glu Gly Asp
            1205                1210                1215

Phe Ser Ala Leu Gly Glu Ile Arg Thr Thr Val Leu Asp Leu Ser Ala
        1220                1225                1230

Pro Ala Gln Leu Val Lys Glu Leu Lys Glu Lys Met Gln Gly Ser Gly
    1235                1240                1245

Met Pro Trp Pro Gly Asp Glu Gly Pro Lys Arg Trp Glu Gln Ala Trp
1250                1255                1260

Met Ala Ile Lys Lys Val Trp Ala Ser Lys Trp Asn Glu Arg Ala Tyr
1265                1270                1275                1280

Phe Ser Thr Arg Lys Val Lys Leu Asp His Asp Tyr Leu Cys Met Ala
            1285                1290                1295

Val Leu Val Gln Glu Ile Ile Asn Ala Asp Tyr Ala Phe Val Ile His
        1300                1305                1310

Thr Thr Asn Pro Ser Ser Gly Asp Asp Ser Glu Ile Tyr Ala Glu Val
    1315                1320                1325

Val Arg Gly Leu Gly Glu Thr Leu Val Gly Ala Tyr Pro Gly Arg Ala
1330                1335                1340

Leu Ser Phe Ile Cys Lys Lys Asp Leu Asn Ser Pro Gln Val Leu
1345                1350                1355                1360

Gly Tyr Pro Ser Lys Pro Ile Gly Leu Phe Ile Lys Arg Ser Ile Ile
            1365                1370                1375

Phe Arg Ser Asp Ser Asn Gly Glu Asp Leu Glu Gly Tyr Ala Gly Ala
        1380                1385                1390

Gly Leu Tyr Asp Ser Val Pro Met Asp Glu Glu Lys Val Val Ile
    1395                1400                1405

Asp Tyr Ser Ser Asp Pro Leu Ile Thr Asp Gly Asn Phe Arg Gln Thr
    1410                1415                1420

Ile Leu Ser Asn Ile Ala Arg Ala Gly His Ala Ile Glu Glu Leu Tyr
1425                1430                1435                1440

Gly Ser Pro Gln Asp Ile Glu Gly Val Val Arg Asp Gly Lys Ile Tyr
            1445                1450                1455

Val Val Gln Thr Arg Pro Gln Met
        1460

(2) INFORMATION FOR SEQ ID NO: 3:

(i) SEQUENCE CHARACTERISTICS:
        (A) LENGTH: 1918 base pairs
        (B) TYPE: nucleotide
        (C) STRANDEDNESS: single
        (D) TOPOLOGY: linear (ii) MOLECULE TYPE: cDNA to mRNA
```

(vi) ORIGINAL SOURCE:
    (A) ORGANISM: Solanum tuberosum
    (B) STRAIN: C.V. Desiree (ix) FEATURE:
    (A) NAME/KEY: CDS
    (B) LOCATION:1..1555

(xi) SEQUENCE DESCRIPTION: SEQ ID NO: 3:

| | | | | | | | | | | | | | | | | |
|---|---|---|---|---|---|---|---|---|---|---|---|---|---|---|---|---|
| GCA | GAG | TGG | TAC | CAT | CAC | TTA | TTG | CAG | CCA | TCT | GCC | GAA | TAT | CTA | GGA | 48 |
| Ala | Glu | Trp | Tyr | His | His | Leu | Leu | Gln | Pro | Ser | Ala | Glu | Tyr | Leu | Gly | |
| 1 | | | | 5 | | | | | 10 | | | | | 15 | | |
| TCA | ATA | CTT | GGG | GTG | GAC | CAA | TGG | GCT | TTG | AAC | ATA | TTT | ACT | GAA | GAA | 96 |
| Ser | Ile | Leu | Gly | Val | Asp | Gln | Trp | Ala | Leu | Asn | Ile | Phe | Thr | Glu | Glu | |
| | | | 20 | | | | | 25 | | | | | 30 | | | |
| ATT | ATA | CGT | GCT | GGA | TCA | GCA | GCT | TCA | TTA | TCC | TCT | CTT | CTT | AAT | AGA | 144 |
| Ile | Ile | Arg | Ala | Gly | Ser | Ala | Ala | Ser | Leu | Ser | Ser | Leu | Leu | Asn | Arg | |
| | | 35 | | | | | 40 | | | | | 45 | | | | |
| CTC | GAT | CCC | GTG | CTT | CGG | AAA | ACT | GCA | AAT | CTA | GGA | AGT | TGG | CAG | ATT | 192 |
| Leu | Asp | Pro | Val | Leu | Arg | Lys | Thr | Ala | Asn | Leu | Gly | Ser | Trp | Gln | Ile | |
| 50 | | | | | 55 | | | | | 60 | | | | | | |
| ATC | AGT | CCA | GTT | GAA | GCC | GTT | GGA | TAT | GTT | GTC | GTT | GTG | GAT | GAG | TTG | 240 |
| Ile | Ser | Pro | Val | Glu | Ala | Val | Gly | Tyr | Val | Val | Val | Val | Asp | Glu | Leu | |
| 65 | | | | 70 | | | | | 75 | | | | | 80 | | |
| CTT | TCA | GTT | CAG | AAT | GAA | ATC | TAC | GAG | AAG | CCC | ACG | ATC | TTA | GTA | GCA | 288 |
| Leu | Ser | Val | Gln | Asn | Glu | Ile | Tyr | Glu | Lys | Pro | Thr | Ile | Leu | Val | Ala | |
| | | | | 85 | | | | | 90 | | | | | 95 | | |
| AAA | TCT | GTT | AAA | GGA | GAG | GAG | GAA | ATT | CCT | GAT | GGT | GCT | GTT | GCC | CTG | 336 |
| Lys | Ser | Val | Lys | Gly | Glu | Glu | Glu | Ile | Pro | Asp | Gly | Ala | Val | Ala | Leu | |
| | | | 100 | | | | | 105 | | | | | 110 | | | |
| ATA | ACA | CCA | GAC | ATG | CCA | GAT | GTT | CTT | TCA | CAT | GTT | TCT | GTT | CGA | GCT | 384 |
| Ile | Thr | Pro | Asp | Met | Pro | Asp | Val | Leu | Ser | His | Val | Ser | Val | Arg | Ala | |
| | | 115 | | | | | 120 | | | | | 125 | | | | |
| AGA | AAT | GGG | AAG | GTT | TGC | TTT | GCT | ACA | TGC | TTT | GAT | CCC | AAT | ATA | TTG | 432 |
| Arg | Asn | Gly | Lys | Val | Cys | Phe | Ala | Thr | Cys | Phe | Asp | Pro | Asn | Ile | Leu | |
| | 130 | | | | | 135 | | | | | 140 | | | | | |
| GCT | GAC | CTC | CAA | GCA | AAG | GAA | GGA | AGG | ATT | TTG | CTC | TTA | AAG | CCT | ACA | 480 |
| Ala | Asp | Leu | Gln | Ala | Lys | Glu | Gly | Arg | Ile | Leu | Leu | Leu | Lys | Pro | Thr | |
| 145 | | | | | 150 | | | | | 155 | | | | | 160 | |
| CCT | TCA | GAC | ATA | ATC | TAT | AGT | GAG | GTG | AAT | GAG | ATT | GAG | CTC | CAA | AGT | 528 |
| Pro | Ser | Asp | Ile | Ile | Tyr | Ser | Glu | Val | Asn | Glu | Ile | Glu | Leu | Gln | Ser | |
| | | | | 165 | | | | | 170 | | | | | 175 | | |
| TCA | AGT | AAC | TTG | GTA | GAA | GCT | GAA | ACT | TCA | GCA | ACA | CTT | AGA | TTG | GTG | 576 |
| Ser | Ser | Asn | Leu | Val | Glu | Ala | Glu | Thr | Ser | Ala | Thr | Leu | Arg | Leu | Val | |
| | | | 180 | | | | | 185 | | | | | 190 | | | |
| AAA | AAG | CAA | TTT | GGT | GGT | TGT | TAC | GCA | ATA | TCA | GCA | GAT | GAA | TTC | ACA | 624 |
| Lys | Lys | Gln | Phe | Gly | Gly | Cys | Tyr | Ala | Ile | Ser | Ala | Asp | Glu | Phe | Thr | |
| | | 195 | | | | | 200 | | | | | 205 | | | | |
| AGT | GAA | ATG | GTT | GGA | GCT | AAA | TCA | CGT | AAT | ATT | GCA | TAT | CTG | AAA | GGA | 672 |
| Ser | Glu | Met | Val | Gly | Ala | Lys | Ser | Arg | Asn | Ile | Ala | Tyr | Leu | Lys | Gly | |
| | 210 | | | | | 215 | | | | | 220 | | | | | |
| AAA | GTG | CCT | TCC | TCG | GTG | GGA | ATT | CCT | ACG | TCA | GTA | GCT | CTT | CCA | TTT | 720 |
| Lys | Val | Pro | Ser | Ser | Val | Gly | Ile | Pro | Thr | Ser | Val | Ala | Leu | Pro | Phe | |
| 225 | | | | | 230 | | | | | 235 | | | | | 240 | |
| GGA | GTC | TTT | GAG | AAA | GTA | CTT | TCA | GAC | GAC | ATA | AAT | CAG | GGA | GTG | GCA | 768 |
| Gly | Val | Phe | Glu | Lys | Val | Leu | Ser | Asp | Asp | Ile | Asn | Gln | Gly | Val | Ala | |
| | | | | 245 | | | | | 250 | | | | | 255 | | |
| AAA | GAG | TTG | CAA | ATT | CTG | ACA | AAA | AAA | CTA | TCT | GAA | GGA | GAC | TTT | AGC | 816 |
| Lys | Glu | Leu | Gln | Ile | Leu | Thr | Lys | Lys | Leu | Ser | Glu | Gly | Asp | Phe | Ser | |
| | | | 260 | | | | | 265 | | | | | 270 | | | |

```
GCT CTT GGT GAA ATT CGC ACA ACG GTT TTA GAT CTT TCG ACA CCA GCT         864
Ala Leu Gly Glu Ile Arg Thr Thr Val Leu Asp Leu Ser Thr Pro Ala
            275                 280                 285

CAA TTG GTC AAA GAG CTG AAG GAG AAG ATG CAG GGT TCT GGC ATG CCT         912
Gln Leu Val Lys Glu Leu Lys Glu Lys Met Gln Gly Ser Gly Met Pro
        290                 295                 300

TGG CCT GGT GAT GAA GGT CCA AAG CGG TGG GAA CAA GCA TGG ATG GCC         960
Trp Pro Gly Asp Glu Gly Pro Lys Arg Trp Glu Gln Ala Trp Met Ala
305                 310                 315                 320

ATA AAA AAG GTG TGG GCT TCA AAA TGG AAT GAG AGA GCA TAC TTC AGC        1008
Ile Lys Lys Val Trp Ala Ser Lys Trp Asn Glu Arg Ala Tyr Phe Ser
                325                 330                 335

ACA AGG AAG GTG AAA CTG GAT CAT GAC TAT CTG TGC ATG GCT GTC CTT        1056
Thr Arg Lys Val Lys Leu Asp His Asp Tyr Leu Cys Met Ala Val Leu
            340                 345                 350

GTT CAA GAA ATA ATA AAT GCT GAT TAT GCA TTT GTC ATT CAC ACA ACC        1104
Val Gln Glu Ile Ile Asn Ala Asp Tyr Ala Phe Val Ile His Thr Thr
        355                 360                 365

AAC CCA TCT TCC GGA GAC GAC TCA GAA ATA TAT GCC GAG GTG GTC AGG        1152
Asn Pro Ser Ser Gly Asp Asp Ser Glu Ile Tyr Ala Glu Val Val Arg
370                 375                 380

GGC CTT GGG GAA ACA CTT GTT GGA GCT TAT CCA GGA CGT GCT TTG AGT        1200
Gly Leu Gly Glu Thr Leu Val Gly Ala Tyr Pro Gly Arg Ala Leu Ser
385                 390                 395                 400

TTT ATC TGC AAG AAA AAG GAT CTC AAC TCT CCT CAA GTG TTA GGT TAC        1248
Phe Ile Cys Lys Lys Lys Asp Leu Asn Ser Pro Gln Val Leu Gly Tyr
                405                 410                 415

CCA AGC AAA CCG ATC GGC CTT TTC ATA AAA AGA TCT ATC ATC TTC CGA        1296
Pro Ser Lys Pro Ile Gly Leu Phe Ile Lys Arg Ser Ile Ile Phe Arg
            420                 425                 430

TCT GAT TCC AAT GGG GAA GAT TTG GAA GGT TAT GCC GGT GCT GGC CTC        1344
Ser Asp Ser Asn Gly Glu Asp Leu Glu Gly Tyr Ala Gly Ala Gly Leu
        435                 440                 445

TAC GAC AGT GTA CCA ATG GAT GAG GAG GAA AAA GTT GTA ATT GAT TAC        1392
Tyr Asp Ser Val Pro Met Asp Glu Glu Glu Lys Val Val Ile Asp Tyr
450                 455                 460

TCT TCC GAC CCA TTG ATA ACT GAT GGT AAC TTC CGC CAG ACA ATC CTG        1440
Ser Ser Asp Pro Leu Ile Thr Asp Gly Asn Phe Arg Gln Thr Ile Leu
465                 470                 475                 480

TCC AAC ATT GCT CGT GCT GGA CAT GCT ATC GAG GAG CTA TAT GGC TCT        1488
Ser Asn Ile Ala Arg Ala Gly His Ala Ile Glu Glu Leu Tyr Gly Ser
                485                 490                 495

CCT CAA GAC ATT GAG GGT GTA GTG AGG GAT GGA AAG ATT TAT GTC GTT        1536
Pro Gln Asp Ile Glu Gly Val Val Arg Asp Gly Lys Ile Tyr Val Val
            500                 505                 510

CAG ACA AGA CCA CAG ATG T GATTATATTC TCGTTGTATG TTGTTCAGAG            1585
Gln Thr Arg Pro Gln Met
            515

AAGACCACAG ATGTGATCAT ATTCTCATTG TATCAGATCT GTGACCACTT ACCTGATACC      1645

TCCCATGAAG TTACCTGTAT GATTATACGT GATCCAAAGC CATCACATCA TGTTCACCTT      1705

CAGCTATTGG AGGAGAAGTG AGAAGTAGGA ATTGCAATAT GAGGAATAAT AAGAAAAACT      1765

TTGTAAAAGC TAAATTAGCT GGGTATGATA TAGGGAGAAA TGTGTAAACA TTGTACTATA      1825

TATAGTATAT ACACACGCAT TATGTATTGC ATTATGCACT GAATAATATC GCAGCATCAA      1885

AGAAGAAATC CTTTGGGTGG TTTCAAAAAA AAA                                  1918

(2) INFORMATION FOR SEQ ID NO: 4:
```

(i) SEQUENCE CHARACTERISTICS:
    (A) LENGTH: 518 amino acids
    (B) TYPE: amino acid
    (D) TOPOLOGY: linear (ii) MOLECULE TYPE: protein (xi) SEQUENCE DESCRIPTION: SEQ ID NO: 4:

```
Ala Glu Trp Tyr His His Leu Leu Gln Pro Ser Ala Glu Tyr Leu Gly
 1               5                  10                  15

Ser Ile Leu Gly Val Asp Gln Trp Ala Leu Asn Ile Phe Thr Glu Glu
             20                  25                  30

Ile Ile Arg Ala Gly Ser Ala Ser Leu Ser Ser Leu Leu Asn Arg
             35                  40                  45

Leu Asp Pro Val Leu Arg Lys Thr Ala Asn Leu Gly Ser Trp Gln Ile
 50                  55                  60

Ile Ser Pro Val Glu Ala Val Gly Tyr Val Val Val Asp Glu Leu
 65                  70                  75                  80

Leu Ser Val Gln Asn Glu Ile Tyr Glu Lys Pro Thr Ile Leu Val Ala
                 85                  90                  95

Lys Ser Val Lys Gly Glu Glu Glu Ile Pro Asp Gly Ala Val Ala Leu
                100                 105                 110

Ile Thr Pro Asp Met Pro Asp Val Leu Ser His Val Ser Val Arg Ala
                115                 120                 125

Arg Asn Gly Lys Val Cys Phe Ala Thr Cys Phe Asp Pro Asn Ile Leu
130                 135                 140

Ala Asp Leu Gln Ala Lys Glu Gly Arg Ile Leu Leu Leu Lys Pro Thr
145                 150                 155                 160

Pro Ser Asp Ile Ile Tyr Ser Glu Val Asn Glu Ile Glu Leu Gln Ser
                165                 170                 175

Ser Ser Asn Leu Val Glu Ala Glu Thr Ser Ala Thr Leu Arg Leu Val
                180                 185                 190

Lys Lys Gln Phe Gly Gly Cys Tyr Ala Ile Ser Ala Asp Glu Phe Thr
            195                 200                 205

Ser Glu Met Val Gly Ala Lys Ser Arg Asn Ile Ala Tyr Leu Lys Gly
210                 215                 220

Lys Val Pro Ser Ser Val Gly Ile Pro Thr Ser Val Ala Leu Pro Phe
225                 230                 235                 240

Gly Val Phe Glu Lys Val Leu Ser Asp Asp Ile Asn Gln Gly Val Ala
                245                 250                 255

Lys Glu Leu Gln Ile Leu Thr Lys Lys Leu Ser Glu Gly Asp Phe Ser
                260                 265                 270

Ala Leu Gly Glu Ile Arg Thr Thr Val Leu Asp Leu Ser Thr Pro Ala
            275                 280                 285

Gln Leu Val Lys Glu Leu Lys Glu Lys Met Gln Gly Ser Gly Met Pro
290                 295                 300

Trp Pro Gly Asp Glu Gly Pro Lys Arg Trp Glu Gln Ala Trp Met Ala
305                 310                 315                 320

Ile Lys Lys Val Trp Ala Ser Lys Trp Asn Glu Arg Ala Tyr Phe Ser
                325                 330                 335

Thr Arg Lys Val Lys Leu Asp His Asp Tyr Leu Cys Met Ala Val Leu
                340                 345                 350

Val Gln Glu Ile Ile Asn Ala Asp Tyr Ala Phe Val Ile His Thr Thr
            355                 360                 365

Asn Pro Ser Ser Gly Asp Asp Ser Glu Ile Tyr Ala Glu Val Val Arg
```

-continued

```
              370                 375                 380
Gly Leu Gly Glu Thr Leu Val Gly Ala Tyr Pro Gly Arg Ala Leu Ser
385                 390                 395                 400

Phe Ile Cys Lys Lys Lys Asp Leu Asn Ser Pro Gln Val Leu Gly Tyr
                405                 410                 415

Pro Ser Lys Pro Ile Gly Leu Phe Ile Lys Arg Ser Ile Ile Phe Arg
                420                 425                 430

Ser Asp Ser Asn Gly Glu Asp Leu Glu Gly Tyr Ala Gly Ala Gly Leu
            435                 440                 445

Tyr Asp Ser Val Pro Met Asp Glu Glu Glu Lys Val Val Ile Asp Tyr
    450                 455                 460

Ser Ser Asp Pro Leu Ile Thr Asp Gly Asn Phe Arg Gln Thr Ile Leu
465                 470                 475                 480

Ser Asn Ile Ala Arg Ala Gly His Ala Ile Glu Glu Leu Tyr Gly Ser
                485                 490                 495

Pro Gln Asp Ile Glu Gly Val Val Arg Asp Gly Lys Ile Tyr Val Val
                500                 505                 510

Gln Thr Arg Pro Gln Met
                515
```

PLANTS WHICH SYNTHESIZE A MODIFIED STARCH, PROCESS FOR THE PRODUCTION THEREOF AND MODIFIED STARCH

This application is a divisional of U.S. application Ser. No. 09/045,360, filed Mar. 19, 1998, now U.S. Pat. No. 6,207,880, which is a continuation of International Patent Application No. PCT/EP96/04109, filed Sep. 19, 1996.

The present invention relates to nucleic acid molecules encoding a starch granule-bound protein as well as to methods and recombinant DNA molecules for the production of transgenic plant cells and plants synthesizing a modified starch with modified properties of viscosity and a modified phosphate content. The invention also relates to the transgenic plant cells and plants resulting from these methods and to the starch obtainable from the transgenic plant cells and plants.

The polysaccharide starch, which constitutes one of the most important storage substances in plants, is not only used in the area of foodstuffs but also plays a significant role as a regenerative material in the manufacturing of industrial products. In order to enable the use of this raw material in as many areas as possible, it is necessary to obtain a large variety of substances as well as to adapt these substances to the varying demands of the processing industry.

Although starch consists of a chemically homogeneous basic component, namely glucose, it does not constitute a homogeneous raw material. It is rather a complex mixture of various types of molecules which differ from each other in their degree of polymerization and in the degree of branching of the glucose chains. One differentiates particularly between amylose-starch, a basically non-branched polymer made up of $\alpha$-1,4-glycosidically branched glucose molecules, and amylopectin-starch which in turn is a mixture of more or less heavily branched glucose chains. The branching results from the occurrence of $\alpha$-1,6-glycosidic interlinkings.

The molecular structure of starch which is mainly determined by its degree of branching, the amylose/amylopectin ratio, the average chain-length and the occurrence of phosphate groups is significant for important functional properties of starch or, respectively, its aqueous solutions. Important functional properties are for example solubility of the starch, tendency to retrogradation, capability of film formation, viscosity, colour stability, pastification properties, i.e. binding and gluing properties, as well as cold resistance. The starch granule size may also be significant for the various uses. The production of starch with a high amylose content is particularly significant. Furthermore, modified starch contained in plant cells may, under certain conditions, favorably alter the behavior of the plant cell. For example, it would be possible to decrease the starch degradation during the storage of the starch-containing organs such as seeds and tubers prior to their further processing by, for example, starch extraction. Moreover, there is some interest in producing modified starches which would render plant cells and plant organs containing this starch more suitable for further processing, such as for the production of popcorn or corn flakes from potato or of French fries, crisps or potato powder from potatoes. There is a particular interest in improving the starches in such a way, that they show a reduced "cold sweetening", i.e. a decreased release of reduced sugars (especially glucose) during long-term storage at low temperatures. Specifically potatoes are often stored at temperatures of 4–8° C. in order to minimize the degradation of starch during storage. The reducing sugars released thereby, in particular glucose, lead to undesired browning reactions (so-called Maillard reactions) in the production of French fries and crisps.

Starch which can be isolated from plants is often adapted to certain industrial purposes by means of chemical modifications which are usually time-consuming and expensive. Therefore it is desirable to find possibilities to produce plants synthesizing a starch the properties of which already meet the demands of the processing industry.

Conventional methods for producing such plants are classical breeding methods and the production of mutants. Thus, for example, a mutant was produced from maize synthesizing starch with an altered viscosity (U.S. Pat. No. 5,331,108) and a maize variety (waxy maize) was established by means of breeding the starch of which consists of almost 100% amylopectin (Akasuka and Nelson, J. Biol. Chem. 241 (1966), 2280–2285). Furthermore, mutants of potato and pea have been described which synthesize starches with a high amylose content (70% in maize or up to 50% in pea). These mutants have so far not been characterized on the molecular level and therefore do not allow for the production of corresponding mutants in other starch-storing plants.

Alternatively, plants synthesizing starch with altered properties may be produced by means of recombinant DNA techniques. In various cases, for example, the recombinant modification of potato plants aiming at altering the starch synthesized in these plants has been described (e.g. WO 92/11376; WO 92/14827). However, in order to make use of recombinant DNA techniques, DNA sequences are required the gene products of which influence starch synthesis, starch modification or starch degradation.

Therefore, the problem underlying the present invention is to provide nucleic acid molecules and methods which allow for the alteration of plants in such a way, that they synthesize a starch which differs from starch naturally synthesized in plants with respect to its physical and/or chemical properties, in particular a highly amylose-containing starch, and is therefore more suitable for general and/or particular uses.

This problem is solved by the provision of the embodiments described in the claims.

Therefore, the present invention relates to nucleic acid molecules encoding a protein with the amino acid sequence indicated in Seq ID No. 2. Such proteins are present in the plastids of plant cells, bound to starch granules as well as in free, i.e. soluble form. During the expression of E.coli, the enzyme activity of such proteins leads to an increased phosphorylation of the glycogen synthesized within the cells. The molecular weight of these proteins lies within the range of 140–160 kD if it is assessed by means of a SDS gel electrophoresis.

The present invention further relates to nucleic acid molecules comprising a sequence with the nucleotide sequence indicated in Seq ID No. 1, particularly the coding region indicated in Seq ID No. 1.

Nucleic acid molecules encoding a protein from potato, which in the plastids of the cells is partly granule-bound, and hybridizing to the above-mentioned nucleic acid molecules of the invention or their complementary strand are also the subject matter of the present invention. In this context the term "hybridization" signifies hybridization under conventional hybridizing conditions, preferably under stringent conditions as described for example in Sambrook et al., Molecular Cloning, A Laboratory Manual, $2^{nd}$ Edition (1989) Cold Spring Harbor Laboratory Press, Cold Spring Harbor, N.Y.). These nucleic acid molecules hybridizing with the nucleic acid molecules of the invention may principally be derived from any desired organism (i.e. prokaryotes or eukaryotes, in particular from bacteria, fungi, alga, plants or animal organisms) comprising such nucleic acid molecules. They are preferably derived from monocotyledonous or dicotyledonous plants, particularly from useful plants, and particularly preferred from starch-storing plants.

Nucleic acid molecules hybridizing to the molecules according to the invention may be isolated e.g. from genomic or from cDNA libraries of various organisms.

Thereby, the identification and isolation of such nucleic acid molecules may take place by using the molecules according to the invention or parts of these molecules or, as the case may be, the reverse complement strands of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequence indicated under Seq ID No. 1 or parts thereof. The DNA fragments used as hybridization probe may also be synthetic DNA fragments which were produced by means of the conventional DNA synthesizing methods and the sequence of which is basically identical with that of a nucleic acid molecule of the invention. After identifying and isolating genes hybridizing to the nucleic acid sequences according to the invention, the sequence has to be determined and the properties of the proteins encoded by this sequence have to be analyzed.

Furthermore, the present invention relates to nucleic acid molecules the sequences of which, compared to the sequences of the above-mentioned molecules, are degenerated due to the genetic code and which encode a protein which in the plastids of plant cells is partly granule-bound.

Fragments, derivatives and allelic variants of the above-mentioned nucleic acid molecules, which encode the above-mentioned protein are also the subject matter of the present invention. Thereby, fragments are described as parts of the nucleic acid molecules which are long enough in order to encode the above-described protein. In this context, the term derivative signifies that the sequences of these molecules differ from the sequences of the above-mentioned nucleic acid molecules at one or more positions and exhibit a high degree of homology to the sequences of these molecules. Hereby, homology means a sequence identity of at least 40%, in particular an identity of at least 60%, preferably of more than 80% and still more preferably a sequence identity of more than 90%. The deviations occurring when comparing with the above-described nucleic acid molecules might have been caused by deletion, substitution, insertion or recombination.

Moreover, homology means that functional and/or structural equivalence exists between the respective nucleic acid molecules or the proteins they encode. The nucleic acid molecules, which are homologous to the above-described nucleic acid molecules and represent derivatives of these molecules, are generally variations of these nucleic acid molecules, that constitute modifications which exert the same biological function. These variations may be naturally occurring variations, for example sequences from different organisms, or mutations, whereby these mutations may have occurred naturally or they may have been introduced deliberately. Moreover the variations may be synthetically produced sequences.

The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability, pH-optimum, temperature-optimum etc.

The nucleic acid molecules of the invention may principally be derived from any organism expressing the described proteins. They are preferably derived from plants, in particular from starch-synthesizing or starch-storing plants. Cereals (such as barley, rye, oats, wheat etc.), maize, rice, pea, cassava, potato etc. are particularly preferred. They can also be produced by means of synthesis methods known to the skilled person.

The nucleic acid molecules of the invention may be DNA molecules, such as cDNA or genomic DNA, as well as RNA molecules.

Furthermore, the invention relates to vectors, especially plasmids, cosmids, viruses, bacteriophages and other vectors common in genetic engineering, which contain the above-mentioned nucleic acid molecules of the invention.

In a preferred embodiment the nucleic acid molecules contained in the vectors are linked to regulatory elements that ensure the transcription and synthesis of a translatable RNA in prokaryotic and eukaryotic cells.

In a further embodiment the invention relates to host cells, in particular prokaryotic or eukaryotic cells, which have been transformed and/or recombinantly manipulated by an above-mentioned nucleic acid molecule of the invention or by a vector of the invention, as well as cells derived from such cells and containing a nucleic acid molecule of the invention or a vector of the invention. This is preferably a bacterial cell or a plant cell.

It was now found that the protein encoded by the nucleic acid molecules of the invention influences the starch synthesis or modification and that changes in the amount of the protein in plant cells lead to changes in the starch metabolism of the plant, especially to the synthesis of starch with modified physical and chemical properties.

By providing the nucleic acid molecules of the invention it is possible to produce plants by means of recombinant DNA techniques synthesizing a modified starch which differs from the starch synthesized in wildtype plants with respect to its structure and its physical and chemical properties. For this purpose, the nucleic acid molecules of the invention are linked to regulatory elements, which ensure the transcription and translation in plant cells, and they are introduced into the plant cells.

Therefore, the present invention also relates to transgenic plant cells containing a nucleic acid molecule of the invention whereby the same is linked to regulatory elements which ensure the transcription in plant cells. The regulatory elements are preferably heterologous with respect to the nucleic acid molecule.

By means of methods known to the skilled person the transgenic plant cells can be regenerated to whole plants. The plants obtainable by regenerating the transgenic plant cells of the invention are also the subject-matter of the present invention. A further subject-matter of the invention are plants which contain the above-described transgenic plant cells. The transgenic plants may in principle be plants of any desired species, i.e. they may be monocotyledonous as well as dicotyledonous plants. These are preferably useful plants, in particular starch-storing plants such as cereals (rye, barley, oats, wheat etc.), rice, maize, peas, cassava and potatoes.

Due to the expression or the additional expression of a nucleic acid molecule of the invention, the transgenic plant cells and plants of the invention synthesize a starch which is modified when compared to starch from wildtype-plants, i.e. non-transformed plants, particularly with respect to the viscosity of aqueous solutions of this starch and/or to the phosphate content. The latter is generally increased in the starch of transgenic plant cells or plants, this altering the physical properties of the starch.

Therefore, the starch obtainable from the transgenic plant cells and plants of the invention is also the subject-matter of the present invention.

A further subject-matter of the present invention is a method for the production of a protein which is present in plant cells in granule-bound form as well as in soluble from, in which host cells of the invention are cultivated under conditions that allow for the expression of the protein and in which the protein is then isolated from the cultivated cells and/or the culture medium.

Furthermore, the invention relates to proteins encoded by the nucleic acid molecules of the invention as well as to proteins obtainable by the above-described method. These are preferably proteins encoded by nuclear genes and which are localized in the plastids. In the plastids these enzymes are present in granule-bound as well as in free form. In an SDS gel electrophoresis, the respective proteins from *Solanum tuberosum* exhibit a molecular weight of 140–160 kD and, during the expression of *E.coli*, lead to an increased phosphorylation of the glycogen synthesized within the cells.

A further subject-matter of the invention are antibodies which specifically recognize a protein of the invention. These may be monoclonal as well as polyclonal antibodies.

Furthermore, the present invention relates to nucleic acid molecules specifically hybridizing with a nucleic acid molecule of the invention and exhibiting a length of at least 15 nucleotides. In this context specifically hybridizing signifies that under conventional hybridization conditions, preferably under stringent conditions, cross-hybridization with sequences encoding other proteins does not significantly occur. Such nucleic acid molecules preferably have a length of at least 20, more preferably a length of at least 50 and most preferably a length of at least 100 nucleotides. Such molecules can be used, for example, as PCR primers, as hybridization probes or as DNA molecules which encode antisense RNA.

Furthermore, it was found that it is possible to influence the properties of the starch synthesized in plant cells by reducing the amount of proteins encoded by the nucleic acid molecules according to the invention in the cells. This reduction may be effected, for example, by means of antisense expression of the nucleic acid molecules of the invention, expression of suitable ribozymes or cosuppression.

Therefore, DNA molecules encoding an antisense RNA which is complementary to transcripts of a DNA molecule of the invention are also the subject-matter of the present invention, as well as these antisense molecules. Thereby, complementary does not signify that the encoded RNA has to be 100% complementary. A low degree of complementarity is sufficient, as long as it is high enough in order to inhibit the expression of a protein of the invention upon expression in plant cells. The transcribed RNA is preferably at least 90% and most preferably at least 95% complementary to the transcript of the nucleic acid molecule of the invention. In order to cause an antisense-effect during the transcription in plant cells such DNA molecules have a length of at least 15 bp, preferably a length of more than 100 bp and most preferably a length of more than 500 bp, however, usually less than 5000 bp, preferably shorter than 2500 bp.

The invention further relates to DNA molecules which, during expression in plant cells, lead to the synthesis of an RNA which in the plant cells due to a cosupression-effect reduces the expression of the nucleic acid molecules of the invention encoding the described protein. The principle of the cosupression as well as the production of corresponding DNA sequences is precisely described, for example, in WO 90/12084. Such DNA molecules preferably encode a RNA having a high degree of homology to transcripts of the nucleic acid molecules of the invention. It is, however, not absolutely necessary that the coding RNA is translatable into a protein.

In a further embodiment the present invention relates to DNA molecules encoding an RNA molecule with ribozyme activity which specifically cleaves transcripts of a DNA molecule of the invention as well as these encoded RNA molecules.

Ribozymes are catalytically active RNA molecules capable of cleaving RNA molecules and specific target sequences. By means of recombinant DNA techniques it is possible to alter the specificity of ribozymes. There are various classes of ribozymes. For practical applications aiming at the specific cleavage of the transcript of a certain gene, use is preferably made of representatives of two different groups of ribozymes. The first group is made up of ribozymes which belong to the group I intron ribozyme type. The second group consists of ribozymes which as a characteristic structural feature exhibit the so-called "hammerhead" motif. The specific recognition of the target RNA molecule may be modified by altering the sequences flanking this motif. By base pairing with sequences in the target molecule these sequences determine the position at which the catalytic reaction and therefore the cleavage of the target molecule takes place. Since the sequence requirements for an efficient cleavage are extremely low, it is in principle possible to develop specific ribozymes for practically each desired RNA molecule.

In order to produce DNA molecules encoding a ribozyme which specifically cleaves transcripts of a DNA molecule of the invention, for example a DNA sequence encoding a catalytic domain of a ribozyme is bilaterally linked with DNA sequences which are homologous to sequences of the target enzyme.

Sequences encoding the catalytic domain may for example be the catalytic domain of the satellite DNA of the SCMo virus (Davies et al., Virology 177 (1990), 216–224) or that of the satellite DNA of the TobR virus (Steinecke et al., EMBO J. 11 (1992), 1525–1530; Haseloff and Gerlach, Nature 334 (1988), 585–591). The DNA sequences flanking the catalytic domain are preferably derived from the above-described DNA molecules of the invention.

In a further embodiment the present invention relates to vectors containing the above-described DNA molecules, in particular those in which the described DNA molecules are linked with regulatory elements ensuring the transcription in plant cells.

Furthermore, the present invention relates to host cells containing the described DNA molecules or vectors. The host cell may be a prokaryotic cell, such as a bacterial cell, or a eukaryotic cell. The eucaryotic host cells are preferably plant cells.

Furthermore, the invention relates to transgenic plant cells containing an above-described DNA molecule encoding an antisense-RNA, a ribozyme or an RNA which leads to a cosuppression effect, whereby the DNA molecule is linked to DNA elements ensuring the transcription in plant cells. These transgenic plant cells may be regenerated to whole plants according to well-known techniques. Thus, the invention also relates to plants which may be obtained through regeneration from the described transgenic plant cells, as well as to plants containing the described transgenic plant cells. The transgenic plants themselves may be plants of any desired plant species, preferably useful plants, particularly starch-storing ones, as indicated above.

Due to the expression of the described DNA molecules encoding antisense RNA, a ribozyme or a cosupression RNA in the transgenic plant cells the amount of proteins encoded by the DNA molecules of the invention which are present in the cells in endogenic form, is reduced. Surprisingly, this reduction leads to a drastic change of the physical and chemical properties of the starch synthesized in the plant cells, in particular with respect to the viscous properties of the aqueous solutions of this starch, to the phosphate content as well as to the release of reducing sugars in the storage of the plant cells or plant parts at low temperatures. The properties of the starch synthesized in the transgenic plant cells is explicitely described below.

Thus, the starch obtainable from the described transgenic plant cells and plants is also the subject matter of the present invention.

Furthermore, the invention relates to the antisense RNA molecules encoded by the described DNA molecules, as well as to RNA molecules with ribozyme activity and RNA molecules which lead to a cosupression effect which are obtainable, for example, by means of transcription.

A further subject-matter of the invention is a method for the production of transgenic plant cells, which in comparison to non-transformed cells synthesize a modified starch. In this method the amount of proteins encoded by the DNA molecules of the invention, which are present in the cells in endogenic form, is reduced in the plant cells.

In a preferred embodiment this reduction is effected by means of an antisense effect. For this purpose the DNA molecules of the invention or parts thereof are linked in antisense orientation with a promoter ensuring the transcription in plant cells and possibly with a termination signal ensuring the termination of the transcription as well as the polyadenylation of the transcript. In order to ensure an efficient antisense effect in the plant cells the synthesized antisense RNA should exhibit a minimum length of 15 nucleotides, preferably of at least 100 nucleotides and most preferably of more than 500 nucleotides. Furthermore, the DNA sequence encoding the antisense RNA should be homologous with respect to the plant species to be transformed. However, DNA sequences exhibiting a high degree of homology to DNA sequences which are present in the cells in endogenic form may also be used, preferably with an homology of more than 90% and most preferably with an homology of more than 95%.

In a further embodiment the reduction of the amount of proteins encoded by the DNA molecules of the invention is effected by a ribozyme effect. The basic effect of ribozymes as well as the construction of DNA molecules encoding such RNA molecules have already been described above. In order to express an RNA with ribozyme activity in transgenic cells the above described DNA molecules encoding a ribozyme are linked with DNA elements which ensure the transcription in plant cells, particularly with a promoter and a termination signal. The ribozymes synthesized in the plant cells lead to the cleavage of transcripts of DNA molecules of the invention which are present in the plant cells in endogenic form.

A further possibility in order to reduce the amount of proteins encoded by the nucleic acid molecules of the invention is cosuppression. Therefore, the plant cells obtainable by the method of the invention are a further subject matter. These plant cells are characterized in that their amount of proteins encoded by the DNA molecules of the invention is reduced and that in comparison to wildtype cells they synthesize a modified starch.

Furthermore, the invention relates to plants obtainable by regeneration of the described plant cells as well as to plants containing the described cells of the invention.

The starch obtainable from the described plant cells and plants is also the subject-matter of the present invention. This starch differs from starch obtained from non-transformed cells or plants in its physical and/or chemical properties. When compared to starch from wildtype plants, the starch exhibits a reduced phosphate content. Moreover, the aqueous solutions of this starch exhibit modified viscous properties.

In a preferred embodiment the phosphate content of the described starch is reduced by at least 50%, more preferably by at least 75% and in a particularly preferred embodiment by more than 80% in comparison to starch derived from wildtype plants.

The modified viscosity of the aqueous solution of this starch is its most advantageous feature.

A well-established test for determining the viscosity is the so-called Brabender test. This test is carried out by using an appliance which is for example known as viscograph E. This equipment is produced and sold, among others, by Brabender fOHG Duisburg (Germany).

The test basically consists in first heating starch in the presence of water in order to assess when hydratization and the swelling of the starch granules takes place. This process which is also named gelatinization or pastification is based on the dissolving the hydrogen bonds and involves a measurable increase of the viscosity in the starch suspension. While further heating after gelatinization leads to the complete dissolving of the starch particles and to a decrease of viscosity, the immediate cooling after gelatinization typically leads to a increase in the viscosity (see FIG. 3). The result of the Brabender test is a graph which shows the viscosity depending on time, whereby at first the solution is heated to above the gelatinization temperature and then cooled.

The analysis of the Brabender graph is generally directed to determining the pastification temperature, the maximum viscosity during heating, the increase in viscosity during cooling, as well as the viscosity after cooling. These parameters are important characteristics when it comes to the quality of a starch and the possibilty to use it for various purposes.

The starch which may for example be isolated from potato plants in which the amount of proteins of the invention within the cells was reduced by means of an antisense effect, showed characteristics strongly deviating from the characteristics of starch isolated from wildtype plants. Compared with these it only shows a low increase in viscosity during heating, a low maximum viscosity as well as a stronger increase in viscosity during cooling (see FIGS. 3, 4 and 5).

In a preferred embodiment the invention relates to starch, the aqueous solutions of which exhibit the characteristic viscous properties depicted in FIG. 4 or 5. Particularly under the conditions mentioned in Example 8a for determining the viscosity with the help of a Brabender viscosimeter, the modified starch, when compared to wildtype plants, exhibits the characteristic of only a low increase in viscosity when heating the solution. This offers the opportunity of using the starch for the production of highly-concentrated glues.

Moreover, after reaching maximum viscosity, there is only a low decrease in viscosity in the case of the modified starch. On the other hand the viscosity increases strongly on cooling; thus, the viscosity of modified starch is higher than the viscosity of starch from wildtype plants.

By reducing the amount of proteins of the invention in transgenic plant cells it is furthermore possible to produce a starch which has the effect that when plant parts containing this starch are stored at low temperatures, in particular at 4–8° C., less reducing sugars are released than is the case which starch from non-transformed cells. This property is particularly advantageous, for example, for providing potatoes which during storage at low temperatures release less reducing sugars and thus exhibit a reduced cold sweetening. Such potatoes are particularly suitable for producing French fries, crisps or similar products since undesirable browning-reactions (Maillard reactions) are avoided or at least strongly reduced during use.

In a particularly preferred embodiment of the present invention not only the synthesis of a protein of the invention is reduced in the transformed plant cells, but moreover also the synthesis of at least one further enzyme involved in starch synthesis and/or modification. In this context, for example, starch granule-bound starch synthases or branching enzymes are preferred. Surprisingly, it was found that potato plants in which the synthesis of the proteins of the invention as well as of the branching enzyme is reduced due to an antisense effect synthesize a starch which in its properties strongly deviates from starch of wildtype plants.

When compared to wildtype starch, the aqueous solutions of this modified starch show almost no increase in viscosity during heating or cooling (cf. FIG. 6).

Furthermore, a microscopical analysis of the starch granules before and after heating clearly shows that, when compared to wildtype plants, the starch granules of plants modified in such a way are not open but remain basically unchanged in their structure. Thus, this is a starch which is resistent to the heating process. If the amylose content of this starch is determined by means of the method described in the Examples, amylose contents of more than 50%, preferably of more than 60% and most preferably of more than 70% are measured for this starch. The aqueous solutions of the starch isolated from this plants preferably show the characteristic viscous properties depicted in FIG. 6.

Such a highly amylose-containing starch of the invention offers a number of advantages for various uses when compared to wildtype plants. Thus, highly amylose-containing starches have a high potential for the use in foils and films. The foils and films produced on the basis of highly amylose-containing starches, which may be used in wide areas of the packaging industry, have the essential advantage of being biodegradable. Apart from this use which is basically covered by classical, petrochemically produced polymers, amylose has further unique fields of application which are caused by the amylose's property to form helices. The helix formed by the amylose is internally hydrophobic and externally hydrophilic. Due to this, amylose may be used for the complexation and molecular encapsulation of low molecular or also of high molecular substances. Examples therefore are:

the molecular encapsulation of vitamines and substances for the protection against oxidation, volatilization, thermal degradation or the transition into an aqueous environment;

the molecular encapsulation of aromatic substances for increasing the solubility;

the molecular encapsulation of fertilizers/pesticides for stabilization and controlled release;

the molecular encapsulation of medical substances for stabilizing the dosage-control and for the controlled release of retarding preparations.

Another important property of amylose is the fact that it is a chiral molecule. Due to the chirality it may preferably be used after immobilization, e.g. on a column for separating enantiomers.

Furthermore, it was surprisingly found that starch which may be isolated from potato plants in which the amount of proteins of the invention in the cells was reduced due to an antisense effect, in combination with a reduction of the proteins exhibiting the enzymatic activity of a starch granule-bound starch synthase of the isotype I (GBSSI) exhibits characteristics which strongly deviate from the characteristics of starch which may be isolated from wildtype plants. When compared to starch from wildtype plants, the aqueous solutions of this starch only show a low increase in viscosity during heating, a low maximum viscosity as well as almost no increase in viscosity during cooling (cf. FIG. 7). If the amylose/amylopectin ratio of this starch is determined, this starch is characterized in that almost no amylose can be measured. The amylose content of this starch is preferably below 5% and most preferably below 2%. The starch of the invention furthermore differs from the known starch which may be produced in transgenic potato plants by inhibiting the GBSSI gene solely by means of recombinant DNA techniques. Thus, this starch shows a strong increase in viscosity during heating. The aqueous solutions of the starch of the invention preferably show the characteristic viscous properties depicted in FIG. 7. Particularly under the conditions for determining the viscosity by means of a Rapid Visco Analyser described in Example 13, the modified starch has the characteristic of only exhibiting a low viscosity increase during heating when compared to wildtype starch, but also when compared to waxy starch. This offers the opportunity to use the starch of the invention for the production of highly-concentrated glues. The modified starch furthermore has the property that there is only a low decrease of viscosity after reaching the maximum viscosity, as well as almost no increase in viscosity during cooling.

Possibilities in order to reduce the activity of a branching enzyme in plant cells were already described, for example in WO 92/14827 and WO 95/26407. The reduction of the activity of a starch granule-bound starch synthase of the isotype I (GBSSI) may be carried out by using methods known to the skilled person, e.g. by means of an antisense effect. DNA sequences encoding a GBSSI from potatoe are for example known from Hegersberg (dissertation (1988) University of Cologne), Visser et al. (Plant Sci. 64 (1989), 185–192) or van der Leiy et al. (Mol. Gen. Genet. 228 (1991), 240–248).

The method of the invention may in principle be used for any kind of plant species. Monocotyledonous and dicotyledonous plants are of interest, in particular useful plants and preferably starch-storing plants such as cereals (rye, barley, oats, wheat etc.), rice, maize, pea, cassava and potatoes.

Within the framework of the present invention the term "regulatory DNA elements ensuring the transcription in plant cells" are DNA regions which allow for the initiation or the termination of transcription in plant cells. DNA regions ensuring the initiation of transcription are in particular promoters.

For the expression of the various above-described DNA molecules of the invention in plants any promoter functioning in plant cells may be used. The promoter may be homologous or heterologous with respect to the used plant species. Use may, for example, be made of the 35S promoter of the cauliflower mosaic virus (Odell et al., Nature 313 (1985), 810–812) which ensures a constitutive expression in all plant tissues and also of the promoter construct described in WO/9401571. However, use may also be made of promoters which lead to an expression of subsequent sequences only at a point of time determined by exogenous factors (such as in WO/9307279) or in a particular tissue of the plant (see e.g. Stockhaus et al., EMBO J. 8 (1989), 2245–2251). Promoters which are active in the starch-storing parts of the plant to be transformed are preferably used. In the case of potato these parts are the potato seeds, in the case of potatoes the tubers. In order to transform potatoes the tuber-specific B33-promoter (Rocha-Sosa et al., EMBO J. 8 (1989), 23–29) may be used particularly, but not exclusively.

Apart from promoters, DNA regions initiating transcription may also contain DNA sequences ensuring a further increase of transcription, such as the so-called enhancer-elements.

Furthermore, the term "regulatory DNA elements" may also comprise termination signals which serve to correctly end the transcription and to add a poly-A-tail to the transcript which is believed to stabilize the transcripts. Such elements are described in the literature and can be exchanged as desired. Examples for such termination sequences are the 3'-nontranslatable regions comprising the polyadenylation signal of the nopaline synthase gene (NOS gene) or the octopine synthase gene (Gielen et al., EMBO J. 8 (1989), 23–29) from agrobacteria, or the 3'-nontranslatable regions of the genes of the storage proteins from soy bean as well as the genes of the small subunit of ribulose-1,5-biphosphate-carboxylase (ssRUBISCO).

The introduction of the DNA molecules of the invention into plant cells is preferably carried out using plasmids. Plasmids ensuring a stable integration of the DNA into the plant genome are preferred.

In the examples of the present invention use is made of the binary vector pBinAR (Höfgen and Willmitzer, Plant Sci. 66 (1990), 221–230). This vector is a derivative of the binary vector pBin19 (Bevan, Nucl. Acids Res. 12 (1984), 8711–8721), which may commercially be obtained (Clontech Laboratories, Inc. USA).

However, use may be made of any other plant transformation vector which can be inserted into a expression cassette and which ensures the integration of the expression cassette into the plant genome.

In order to prepare the introduction of foreign genes in higher plants a large number of cloning vectors are at disposal, containing a replication signal for *E.coli* and a marker gene for the selection of transformed bacterial cells. Examples for such vectors are pBR322, pUC series, M13mp series, pACYC184 etc. The desired sequence may be integrated into the vector at a suitable restriction site. The obtained plasmid is used for the transformation of *E.coli* cells. Transformed *E.coli* cells are cultivated in a suitable medium and subsequently harvested and lysed. The plasmid is recovered by means of standard methods. As an analyzing method for the characterization of the obtained plasmid DNA use is generally made of restriction analysis and sequence analysis. After each manipulation the plasmid DNA may be cleaved and the obtained DNA fragments may be linked to other DNA sequences.

In order to introduce DNA into plant host cells a wide range of techniques are at disposal. These techniques comprise the transformation of plant cells with T-DNA by using *Agrobacterium tumefaciens* or *Agrobacterium rhizogenes* as transformation medium, the fusion of protoplasts, the injection and the electroporation of DNA, the introduction of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of introducing desired genes into the plant cell, further DNA sequences may be necessary. If the Ti- or Ri-plasmid is used e.g. for the transformation of the plant cell, at least the right border, more frequently, however, the right and left border of the Ti- and Ri-plasmid T-DNA has to be connected to the foreign gene to be introduced as a flanking region.

If Agrobacteria are used for transformation, the DNA which is to be introduced must be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to *Agrobacterium tumefaciens* (conjugation). Binary vectors may replicate in *E.coli* as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The plasmids used for the transformation of the Agrobacteria further comprise a selectable marker gene, such as the NPT II gene which allows for selecting transformed bacteria. The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287. Some binary vectors may already be obtained commercially, such as pBIN19 (Clontech Laboratories, Inc., USA).

For transferring the DNA into the plant cells, plant explants may suitably be co-cultivated with *Agrobacterium tumefaciens* or *Agrobacterium rhizogenes*. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the introduced DNA is present or not.

Once the introduced DNA has been integrated in the genome of the plant cell, it usually continues to be stable there and also remains within the descendants of the originally transformed cell. It usually contains a selectable marker which confers resistance against biozides or against an antibiotic such as kanamycin, G 418, bleomycin, hygromycin or phosphinotricine etc. to the transformed plant cells. The individually selected marker should therefore allow for a selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties.

Two or more generations should be grown in order to ensure whether the phenotypic feature is kept stably and whether it is transferred. Furthermore, seeds should be harvested in order to ensure that the corresponding phenotype or other properties will remain.

Due to its properties the starch obtained from the plant cells or from the plants of the invention is not only suitable for the specific purposes already mentioned herein, but also for various industrial uses.

Basically, starch can be subdivided into two major fields. One field comprises the hydrolysis products of starch and the so-called native starches. The hydrolysis products essentially comprise glucose and glucans components obtained by enzymatic or chemical processes. They can be used for further processes, such as fermentation and chemical modifications. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The use of the so-called native starch which is used because of its polymer structure can be subdivided into two further areas:

(a) Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

(b) Use in Non-Foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

Furthermore, starch may be used as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

Furthermore, the starch may be used as a flocculant in the processing of ore and coal slurry.

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

Another field of application for the modified starch is the production of leather substitutes.

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance.

These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity. The most remarkable feature is viscosity.

Moreover, the modified starch obtained from the plant cells of the invention may be subjected to further chemical modification, which will result in further improvement of the quality for certain of the above-described fields of application. These chemical modifications are principally known to the person skilled in the art. These are particularly modifications by means of acid treatment oxidation and esterification (formation of phosphate, nitrate, sulphate, xanthate, acetate and citrate starches. Further organic acids may also be used for esterification.)

formation of starch ethers (starch alkyl ether, O-allyl ether, hydroxylalkyl ether, O-carboxylmethyl ether, N-containing starch ethers, S-containing starch ethers)

formation of branched starches formation of starch graft polymers.

The invention also relates to propagation material of the plants of the invention, such as seeds, fruits, cuttings, tubers or root stocks, wherein this propagation material contains plant cells of the invention.

Deposits

The plasmids produced and/or used within the framework of the present invention have been deposited at the internationally acknowledged deposit "Deutsche Sammlung von Mikroorganismen (DSM)" in Braunschweig, Federal Republic of Germany, according to the requirements of the Budapest treaty for international acknowledgment of microorganism deposits for patenting (deposit number; deposition date):

| plasmid pBinAR Hyg | (DSM 9505) | (10/20/94) |
| plasmid p33-anti-BE | (DSM 6146) | (08/20/90) |
| plasmid pRL2 | (DSM 10225) | (09/04/95) |

Used media and solutions

| Elution buffer: | 25 mM Tris pH 8.3 |
| | 250 mM glycine |
| Dialysis buffer: | 50 mM Tris-HCl pH 7.0 |
| | 50 mM NaCl |
| | 2 mM EDTA |

-continued

Used media and solutions

| | | |
|---|---|---|
| | 14.7 mM | β-mercaptoethanol |
| | 0.5 mM | PMSF |
| Protein buffer: | 50 mM | sodium phosphate buffer pH 7.2 |
| | 10 mM | EDTA |
| | 0.5 mM | PMSF |
| | 14.7 mM | β-mercaptoethanol |
| Lugol solution: | 12 g | KI |
| | 6 g | $I_2$ |
| | ad 1.8 l with $ddH_2O$ | |
| 20 × SSC: | 175.3 g | NaCl |
| | 88.2 g | sodium citrate |
| | ad 1000 ml with $ddH_2O$ | |
| | ph 7.0 with 10 N NaOH | |
| 10 × MEN: | 200 mM | MOPS |
| | 50 mM | sodium acetate |
| | 10 mM | EDTA |
| | pH 7.0 | |
| NSEB buffer: | 0.25 M | sodium phosphate buffer pH 7.2 |
| | 7% | SDS |
| | 1 mM | EDTA |
| | 1% | BSA (w/v) |

Plasmid structure:

A=fragment A: CaMV 35S promoter, nt 6909–7437 (Franck et al., Cell 21 (1980), 285–294)

B=fragment B: Asp718 fragment from pRL1 with a length of approximately 1949 bp
Orientation relative to the promoter: anti-sense
The arrow indicates the direction of the open reading frame.

C=fragment C: nt 11748–11939 of the T-DNA of Ti-plasmid pTiACH5 T-DNA (Gielen et al., EMBO J. 3 (1984), 835–846)

Figure 2:
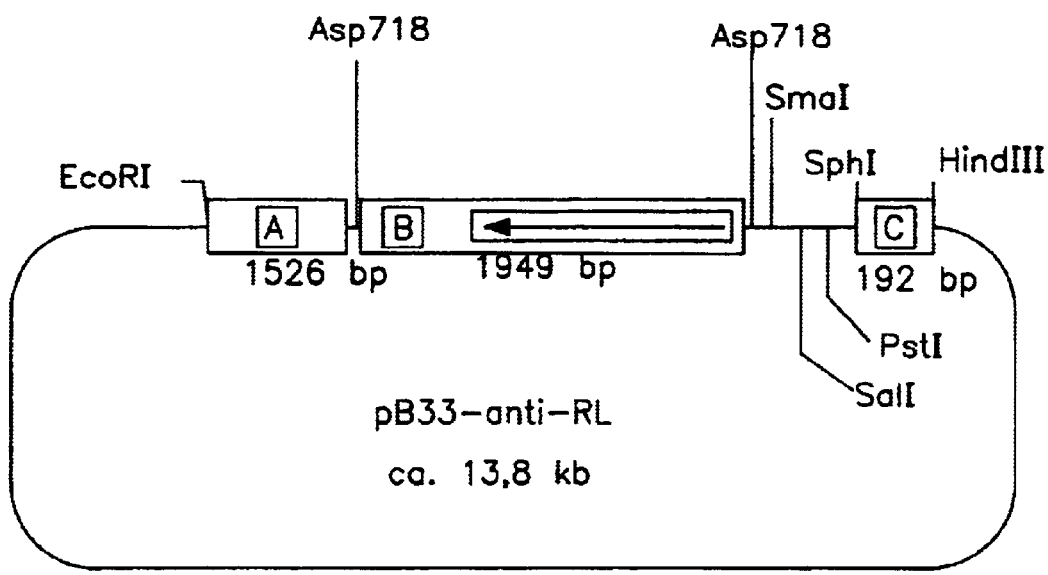

FIG. 2 shows the plasmid pB33-anti-RL

Plasmid structure:

A=fragment A: B33 promoter of the patatin gene B33 from *Solanum tuberosum* (Rocha-Sosa et al., EMBO J. 8 (1989), 23–29)

B=fragment B: Asp718 fragment from pRL1 with a length of approximately 1949 bp
Orientation relative to the promoter: anti-sense
The arrow indicates the direction of the open reading frame.

C=fragment C: nt 11748–11939 of the T-DNA of Ti-plasmid pTiACH5 T-DNA (Gielen et al., EMBO J. 3 (1984), 835–846)

Figure 3:
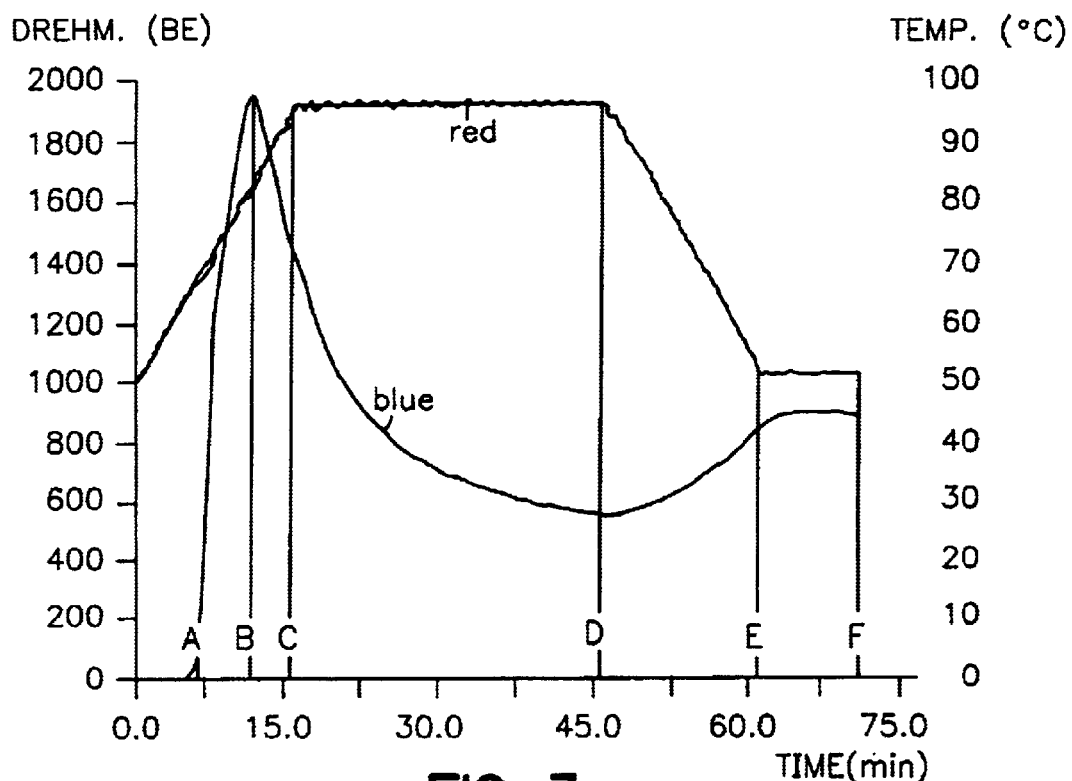

FIG. 3 shows a Brabender curve of a aqueous starch solution, recorded with a Viskograph-E-type Brabender viscograph, which was isolated from non-transformed potato plants of the variety Désirée (see also Example 8).

| Thereby signifying: | Drehm. | torque |
|---|---|---|
| | [BE] | Brabender unit |
| | Temp. | temperature |
| | A | start of pastification |
| | B | maximum degree of viscosity |
| | C | start of the 96° C. period |
| | D | start of the cooling-off period |
| | E | end of the cooling-off period |
| | F | end of the end-50° C. period |

The blue line indicates the viscosity; the red line stands for temperature.

Figure 4:
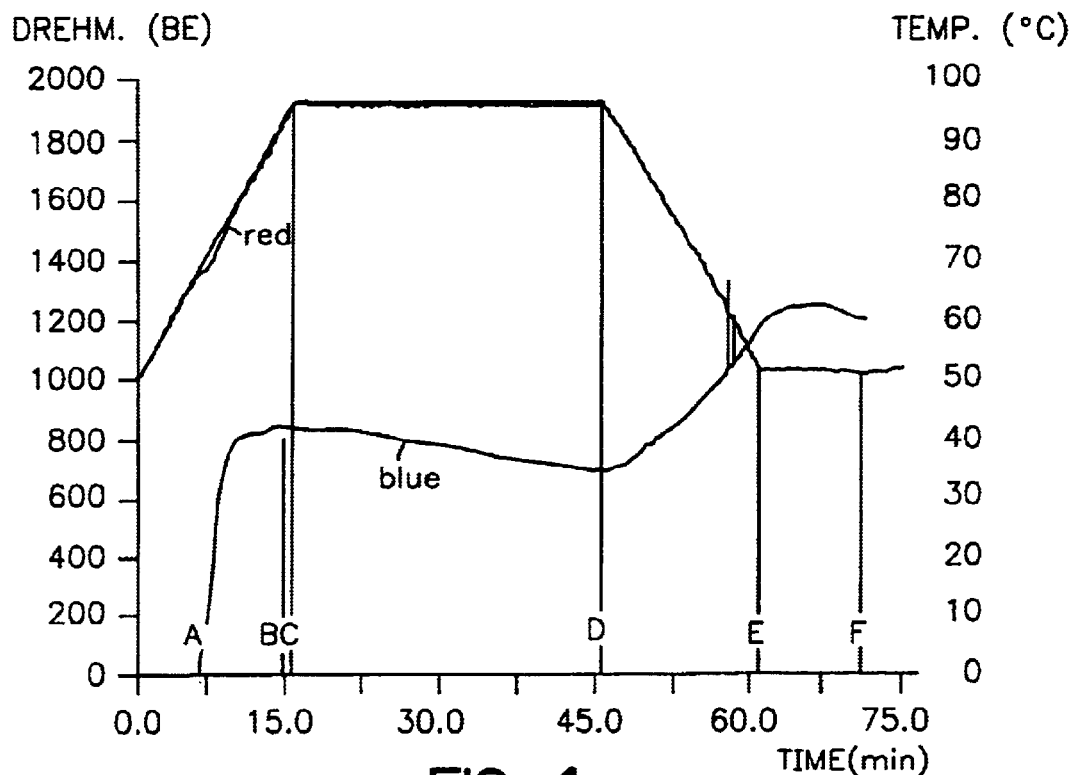

FIG. 4 shows a Brabender curve of a aqueous starch solution, recorded with a Viskograph-E-type Brabender viscograph, which was isolated from potato plants transformed with the plasmid p35S-anti-RL (see also Example 8). For the meaning of the abbreviations see FIG. 3.

Figure 5:
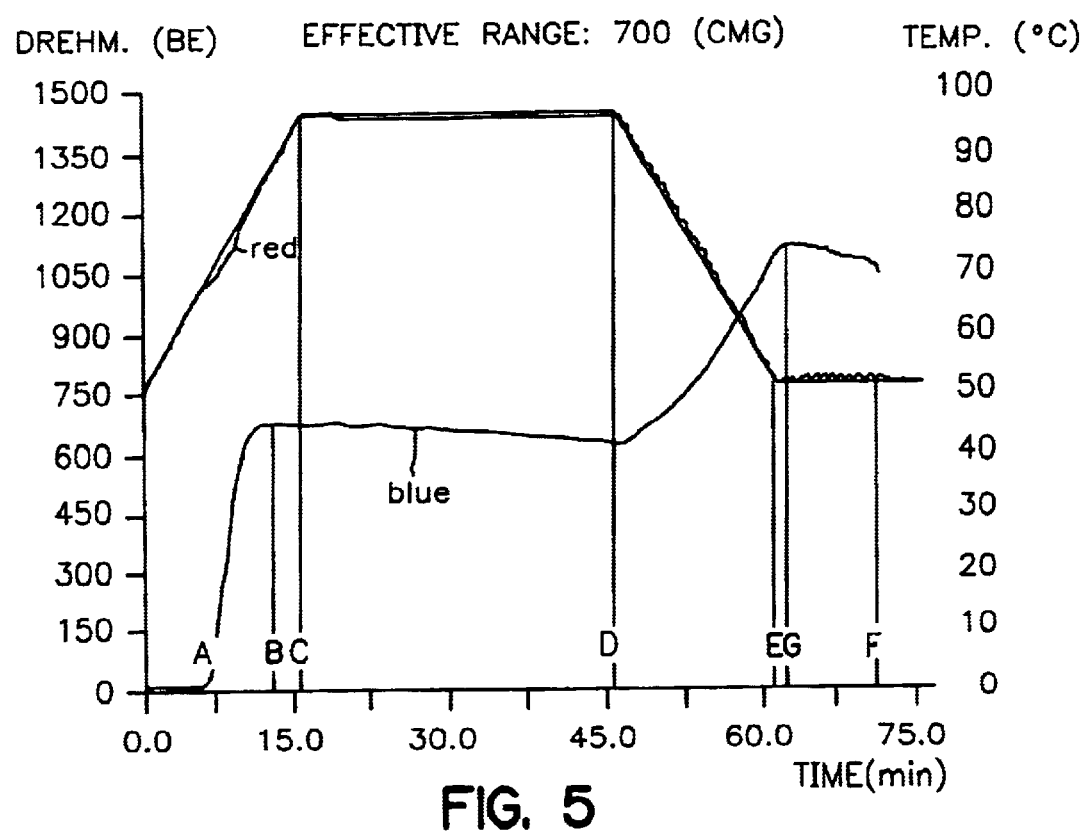

FIG. 5 shows a Brabender curve of a aqueous solution of starch from potatoes transformed with the plasmid pB33-anti-RL (see also Example 8), recorded with a Viskograph-E-type Brabender viscograph. For the meaning of the abbreviations see FIG. 3.

Figure 6:
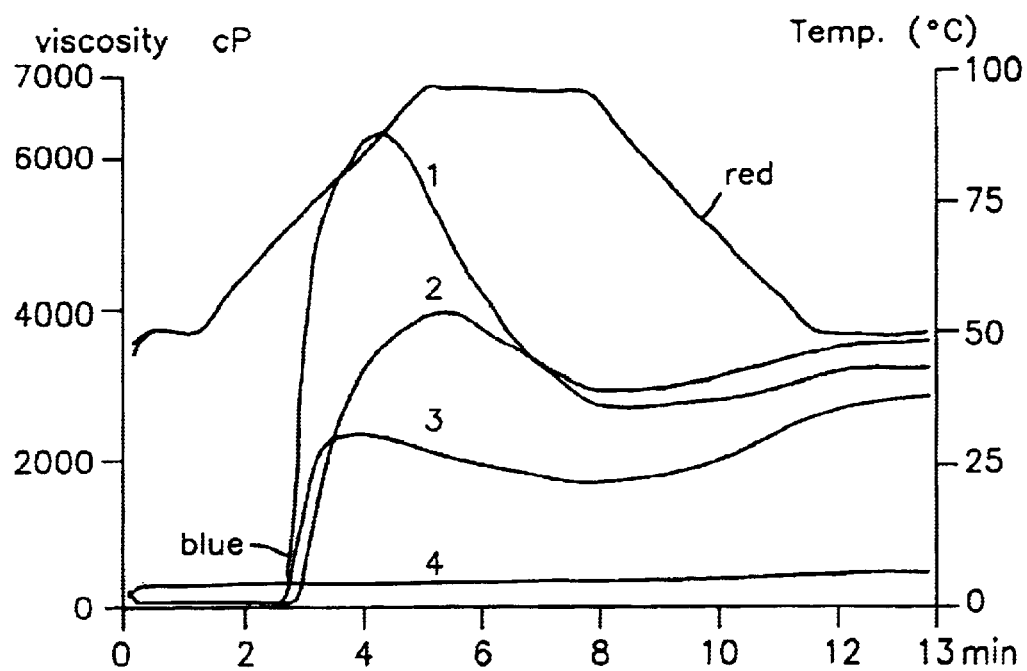

FIG. 6 shows curves of aqueous solutions of starch isolated from potato plants (see also Example 12), which were recorded with a Rapid Visco Analyser. The red line stands for the temperature; the blue lines 1, 2, 3 and 4 show the viscosities of the following starch solutions:

Line 1: starch isolated from wildtype plants,

Line 2: starch isolated from plants in which only the branching enzyme was inhibited (cf. Example 1 of patent application WO92/14827), Line 3: starch isolated from plants in which merely the concentration of the proteins of the invention had been reduced (cf. Example 6).

Line 4: starch isolated from plants which had been transformed with the plasmid p35S-anti-RL in combination with the p35SH-anti-BE plasmid (cf. Example 12).

Figure 7:
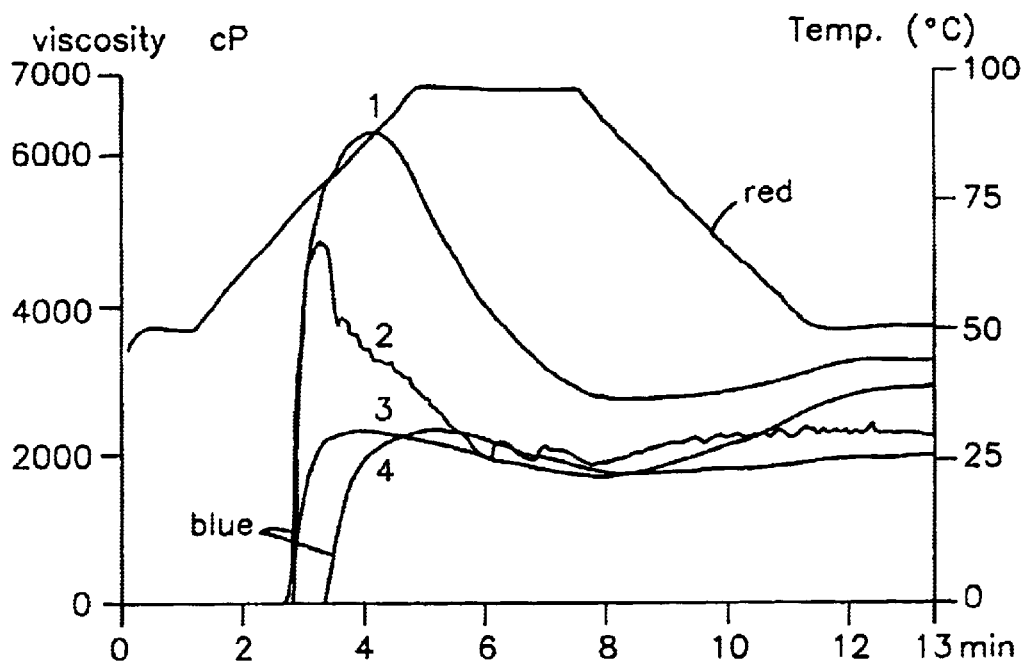

FIG. 7 shows curves of aqueous solutions of starch isolated from potato plants (see also Example 13), which were recorded with a Rapid Visco Analyser. The red line stands for the temperature; the blue lines 1, 2, 3 and 4 show the viscosities of the following starch solutions:

Line 1: starch isolated from wildtype plants,

Line 2: starch isolated from plants which had solely been transformed with the plasmid pB33-anti-GBSSI (so-called waxy-potato), Line 3: starch isolated from plants which had been solely transformed with the plasmid p35S-anti-RL (cf. Example 6).

Line 4: starch isolated from plants which had been transformed with the plasmid pB33-anti-RL in combination with the plasmid pB33-anti-GBSSI (cf. Example 13).

The Examples illustrate the invention.

1. Cloning

For cloning in *E.coli* the vector pBluescriptSK was used.

For plant transformation the gene constructs were cloned into the binary vector pBinAR (Höfgen and Willmitzer, Plant Sci. 66 (1990), 221–230) and B33-Hyg.

2. Bacterial Strains

For the Bluescript vector and for the pBinAR and B33-Hyg constructs use was made of the *E.coli* strain DH5α (Bethesda Research Laboratories, Gaithersburgh, USA).

The transformation of plasmid in potato plants was carried out by means of the *Agrobacterium tumefaciens* strain C58C1 pGV2260 (Deblaere et al., Nucl. Acids Res. 13 (1985), 4777:4788).

3. Transformation of *Agrobacterium tumefaciens*

The DNA transfer was carried out by means of direct transformation according to the method of Höfgen & Willmitzer (Nucleic Acids Res. 16 (1988), 9877). The plasmid DNA of transformed Agrobacteria was isolated according to the method of Birnboim & Doly (Nucleic Acids Res. 7 (1979), 1513–1523) and electrophoretically analyzed after suitable restriction cleavage.

4. Transformation of Potatoes

Ten small leaves of a sterile potato culture (*Solanum tuberosum* L. cv. Désirée) injured by a scalpel were treated with 10 ml MS medium (Murashige & Skoog, Physiol. Plant. 15 (1962), 473–497) with 2% sucrose. The medium contained 50 μl of a *Agrobacterium tumefaciens* overnight-culture grown under selection. After slightly shaking it for 3–5 minutes, another incubation took place in darkness for two days. The leaves were subsequently put on MS medium with 1.6% glucose, 5 mg/l naphthyl acetic acid, 0.2 mg/l benzylaminopurine, 250 mg/l claforan, 50 mg/l kanamycin or 1 mg/l hygromycin B, and 0,80% Bacto Agar for callus induction. After a one-week incubation at 25° C. and 3000 lux the leaves were put on MS-medium with 1.6% glucose, 1.4 mg/l zeatine ribose, 20 mg/l naphthyl acetic acid, 20 mg/l giberellic acid, 250 mg/l claforan, 50 mg/l kanamycin or 3 mg/l hygromycin B and 0.80% Bacto Agar for shoot induction.

5. Radioactive Marking of DNA Fragments

The radioactive marking of DNA fragments was carried out by means of a DNA-Random Primer Labeling Kits by Boehringer (Germany) according to the manufacturer's instructions.

6. Northern Blot Analysis

RNA was isolated from leave tissue according to standard protocols. 50 μg of the RNA was separated on an agarose gel (1.5% agarose, 1×MEN buffer, 16.6% formaldehyde). After the gel run the gel was briefly washed in water. The RNA was transferred to a Hybond N type nylon membrane (Amersham, UK) with 20×SSC by means of capillary blot. The membrane was subsequently baked in vacuum for two hours at 80° C.

The membrane was prehybridized in NSEB buffer for two hours at 68° C. and subsequently hybridized overnight in NSEB buffer in the presence of the radioactively marked probe at 68° C.

7. Plant Maintenance

Potato plants were kept in the greenhouse under the following conditions:

| | |
|---|---|
| light period | 16 hours at 25000 lux and 22° C. |
| dark period | 8 hours at 15° C. |
| atmospheric humidity | 60% |

8. Determination of the Amylose/Amylopectin Ratio in Starch Obtained from Potato Plants Starch was isolated from potato plants according to standard methods and the amylose/amylopectin ratio was determined according to the method described by Hovenkamp-Hermelink et al. (Potato Research 31 (1988) 241–246).

9. Determination of Glucose, Fructose and Sucrose

In order to determine the glucose, fructose and/or sucrose content, small pieces of potato tubers (with a diameter of approx. 10 mm) are frozen in liquid nitrogen and subsequently extracted for 30 min at 80° C. in 0.5 ml 10 mM HEPES, pH 7.5; 80% (vol./vol.) ethanol. The supernatant containing the soluble components is withdrawn and the volume is determined. The supernatant is used for determining the amount of soluble sugars. The quantitative determination of soluble glucose, fructose and sucrose is carried out in a reaction mixture with the following composition:

100.0 mM imidazole/HCl, pH 6.9
1.5 mM $MgCl_2$
0.5 mM $NADP^+$
1.3 mM ATP
10–50 μl sample
1.0 U glucose-6-phosphate dehydrogenase from yeast The reaction mixture is incubated at room temperature for 5 minutes. The subsequent determination of sugars is carried out by means of standard photometric methods by measuring the absorption at 340 nm after successive adding of 1.0 unit of hexokinase from yeast (for determining glucose)

1.0 unit of phosphoglucoisomerase from yeast (for determining fructose) and 1.0 unit of invertase from yeast (for determining sucrose).

EXAMPLE 1

The Isolation of Starch Granule-Bound Proteins from Potato Starch

The isolation of starch granule-bound proteins from potato starch has been carried out by means of electroelution in an elution appliance which was constructed analogous to the "Model 422 Electro Eluter" (BIORAD Laboratories Inc., USA) but had a considerably greater volume (approx. 200 ml). 25 g dried starch were dissolved in elution buffer (final volume 80 ml). The starch was derived from potatoes which produce an almost amylose-free starch due to the antisense-expression of a DNA sequence encoding the starch granule-bound starch synthase I (GBSS I) from potato. The suspension was heated to 70–80° C. in a water bath. Subsequently 72.07 g urea was added (final concentration 8 M) and the volume was filled up to 180 ml with elution buffer. The starch dissolved during permanent stirring and acquired a paste-like consistency. The proteins were electroeluted from the solution overnight by means of the elution appliance (100 V; 50–60 mA). The eluted proteins were carefully removed from the appliance. Suspended particles were removed in a brief centrifugation. The supernatant was dialyzed at 4° C. 2 to 3 times for one hour against dialysis buffer. Subsequently, the volume of the protein solution was determined. The proteins were precipitated by adding ammonium sulfate (final concentration 90%), which was done during permanent stirring at 0° C. The precipitated proteins were pelleted by centrifugation and resuspended in protein buffer.

EXAMPLE 2

Identification and Isolation of cDNA Sequences Encoding Starch Granule-Bound Proteins The proteins isolated according to Example 1 were used for the production of polyclonal antibodies from rabbit, which specifically recognize starch granule-bound proteins.

By means of such antibodies a cDNA expression library was subsequently screened for sequences encoding starch granule-bound proteins, using standard methods.

The expression library was produced as follows:

Poly ($A^+$)-mRNA was isolated from potato tubers of the "Berolina" variety. Starting from the poly ($A^+$)-mRNA, cDNA was produced according to the Gubler and Hoffmann method (Gene 25 (1983), 263–269), using an Xho I-Oligo $d(t)_{18}$ primer. This cDNA was cut with Xho I after EcoR I-linker addition and ligated in an oriented manner in a lambda ZAP II vector (Stratagene) cut with EcoR I and Xho I. Approximately 500,000 plaques of a cDNA library constructed in such a way were screened for sequences which were recognized by polyclonal antibodies directed against starch granule-bound proteins.

In order to analyze the phage plaques these were transferred to nitrocellulose filters which had previously been incubated in a 10 mM IPTG solution for 30 to 60 minutes and had subsequently been dried on filter paper. The transfer took place at 37° C. for 3 hours. Subsequently, the filters are incubated at room temperature for 30 minutes in block reagent and washed for 5–10 minutes in TBST buffer. The filters were shaken with the polyclonal antibodies directed against starch granule-bound proteins in a suitable dilution for one hour at room temperature or for 16 hours at 4° C. The identification of plaques expressing a protein which was recognized by the polyclonal antibodies was carried out by means of the "Blotting detection kit for rabbit antibodies RPN 23" (Amersham UK) according to the manufacturer's instructions.

Phage clones of the cDNA library expressing a protein which was recognized by the polyclonal antibodies were further purified by using standard methods.

By means of the in-vivo excision method, E.coli clones were obtained from positive phage clones containing a double-stranded pBluescript plasmid with the corresponding cDNA insertion. After checking the size and the restriction pattern of the insertions a suitable clone, pRL1, was further analyzed.

EXAMPLE 3

Sequence Analysis of the cDNA Insertion of the Plasmid pRL1

From an E.coli clone obtained according to Example 2 the plasmid pRL1 was isolated and a part of the sequence of its cDNA insertion was determined by standard procedures using the didesoxynucleotide method (Sanger et al., Proc. Natl. Acad. Sci. USA 74 (1977), 5463–5467). The insertion has a length of about 2450 bp. A part of the nucleotide sequence as well as the amino acid sequence derived therefrom is indicated under Seq ID No. 3 and under Seq ID No. 4.

A sequence analysis and a sequence comparison with known DNA sequences showed that the sequence indicated under Seq ID No. 3 is new and exhibits no significant homology to DNA sequences known so far. Moreover, the sequence analysis showed that the cDNA insertion is only a partial cDNA in which a part of the coding region at the 5'-end is missing.

EXAMPLE 4

Identification and Isolation of a Complete cDNA Encoding a Starch Granule-Bound Protein from *Solanum tuberosum*

In order to isolate a complete cDNA corresponding to the partial cDNA insertion of the plasmid pRL1, a further cDNA library was produced. This was a guard-cell-specific cDNA library from *Solanum tuberosum* which was constructed as follows:

At first epidermis fragments from leaves of "Desirée" variety potato plants were produced essentially according to the Hedrich et al. method (Plant Physiol. 89 (1989), 148), by harvesting approximately 60 leaves of six-weeks-old potato plants kept in the greenhouse. The center nerve was removed from the leaves. The leaves were subsequently crushed in a big "Waring blender" (with a volume of 1 liter) four times in cooled, distilled $H_2O$ on the highest level for 15 seconds each. The suspension was filtered through a nylon sieve with a mesh size of 220 µm (Nybolt, Zurich, Switzerland) and washed in cold distilled water several times. The suspension itself was filtered through a 220 µm nylon sieve and intensely washed with cold distilled water. The residues (epidermis fragments) were crushed in a smaller "Waring blender" (with a volume of 250 ml) four times in distilled water and ice on a lower level for 15 seconds each. The suspension was filtered through a 220 µm nylon sieve and washed intensely with cold distilled water. The epidermis fragments (residues) were microscopically examined for contamination by mesophyl cells. If contamination occurred the crushing step was repeated in a small "Waring blender".

The disruption of the guard cells of the epidermis fragments was carried out by means of pulverizing in liquid nitrogen in a cooled mortar for approximately two hours. In order to examine the disruption of the guard cells, probes were regularly taken and microscopically examined. After two hours, or if a sufficiently high amount of guard cells had been disrupted, the obtained powder was filled into a reaction tube (with a volume of 50 ml) and resuspended in one volume GTC buffer (Chirgwin et al., Biochem. 18 (1979), 5294–5299). The suspension was centrifuged and the supernatant was filtered through Miracloth (Calbiochem, La Jolla, Calif.). The filtrate was subjected to ultracentrifugation for 16 hours, as described in Glisin et al. (Biochemistry 13 (1974), 2633–2637) and Mornex et al. (J. Clin. Inves. 77 (1986), 1952–1961). After the centrifugation the RNA precipitate was dissolved in 250 µl GTC buffer. The RNA was precipitated by adding 0.05 volumes of 1 M acetic acid and 0.7 volumes of ethanol. The RNA was precipitated by centrifugation and the precipitate was washed with 3 M sodium acetate (pH 4.8) and 70% ethanol. The RNA was briefly dried and dissolved in DEPC treated water.

Poly $A^+$-RNA was isolated from the isolated RNA according to standard methods. Starting from the poly($A^+$)-mRNA, cDNA was produced according to the Gubler and Hoffmann method (Gene 25 (1983), 263–269) by means of a Xho I-oligo $d(t)_{18}$ primer. This cDNA was cut with Xho I after EcoR I-linker addition and ligated in an oriented manner in a lambda ZAP II vector (Stratagene GmbH, Heidelberg, Germany) cut with EcoR I and Xho I. The packaging in phage heads was carried out using the Gigapack II Gold kit (Stratagene GmbH, Heidelberg, Germany) according to the manufacturer's instructions.

From such a cDNA library phage clones hybridizing with the cDNA insertion of the pRL1 plasmid were isolated and purified according to standard methods. By means of the in vivo excision method E.coli clones were obtained from positive phage clones containing a double-stranded pBluescript plasmid with the corresponding cDNA insertion. After checking the size and the restriction pattern of the insertions, suitable clones were subjected to restriction mapping and sequence analysis. From a suitable clone the plasmid pRL2 (DSM 10225) was isolated which contains a complete cDNA which encodes a starch granule-bound protein from potato.

EXAMPLE 5

Sequence Analysis of the cDNA Insertion of the pRL2 Plasmid

The nucleotide sequence of the cDNA insertion of the pRL2 plasmid was determined as described in Example 3. The insertion has a length of 4856 bp. The nucleotide sequence as well as the amino acid sequence derived therefrom is indicated in Seq ID No. 1 and/or Seq ID No. 2. In the following, the corresponding gene will be called RL-gene.

EXAMPLE 6

The Construction of the Plasmid p35S-anti-RL and the Introduction of the Plasmid into the Genome of Potato Plants By means of the restriction endonuclease Asp718 a DNA fragment with an approximate length of 1800 bp was isolated from the pRL1 plasmid. This corresponds to the DNA sequence indicated under Seq ID No. 3 and contains a part of the open reading frame. The fragment was ligated into the binary vector pBinAR cut with Asp718 (Höfgen and Willmitzer, Plant Sci. 66 (1990), 221–230). This is a derivative of the binary vector pBin19 (Bevan, Nucl. Acids Res. 12 (1984), 8711–8721). pBinAR was constructed as follows:

A fragment with a length of 529 bp comprising the nucleotides 6909–7437 of the 35S promoter of the cauliflower-mosaic virus (Franck et al., Cell 21 (1980), 285–294) was isolated from the plasmid pDH51 (Pietrzak et al., Nucl. Acids Res. 14, 5857–5868) as an EcoR I/Kpn I fragment and ligated between the EcoR I and the Kpn I sites of the pBin19 polylinker. This led to the plasmid pBin19-A.

By means of the restriction-endonucleases Pvu II and Hind III a fragment with a length of 192 bp was isolated from the plasmid pAGV40 (Herrera-Estrella et al., Nature 303, 209–213) comprising the polyadenylation signal of gene 3 of the T-DNA of the Ti-plasmid pTiACH5 (Gielen et al., EMBO J. 3, 835–846) (nucleotides 11749–11939). After the addition of Sph I-linkers to the Pvu I site the fragment was ligated between the Sph I and Hind III sites of pBin19-A. This led to plasmid pBinAR.

Figure 1:
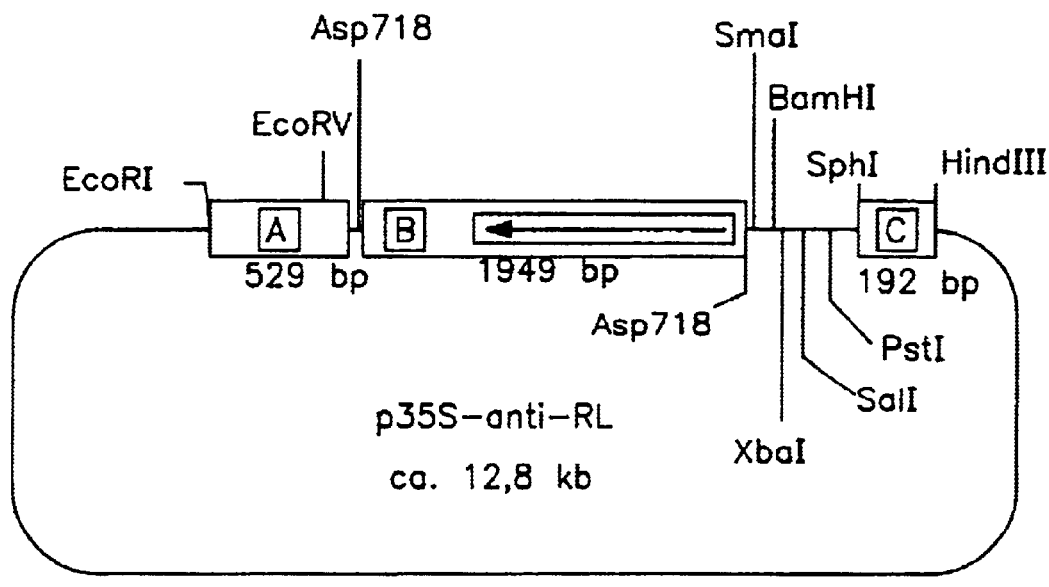
FIG. 1 shows the plasmid p35S-anti-RL.

By means of restriction and sequence analysis recombinant vectors were identified in which the DNA fragment is inserted in the vector in such a way that a part of the coding region of the cDNA insertion from pRL1 is linked with the 35S promoter in antisense orientation. The resulting plasmid p35S-anti-RL is shown in FIG. 1.

By inserting the cDNA fragment an expression cassette is produced which consists of the fragments A, B and C:

Fragment A (529 bp) contains the 35S promoter of the cauliflower-mosaic virus (CaMV). The fragment comprises the nucleotides 6909 to 7437 of the CaMV (Franck et al., Cell 21 (1980), 285–294).

Apart from flanking regions, fragment B contains a part of the protein-encoding areas of the cDNA insertion from plasmid pRL1. This was isolated as an Asp718 fragment of pRL1 as described above and fused to the 35S promoter in antisense orientation. Fragment C (192 bp) contains the polyadenylation signal of gene 3 of the T-DNA of the Ti-plasmid pTiACH5 (Gielen et al., EMBO J. 3 (1984), 835–846).

The plasmid p35S-anti-RL has a size of approximately 12.8 kb. The plasmid was transferred into potato plants by means of Agrobacteria-mediated transformation, as described above. From the transformed cells whole plants were regenerated. The transformed plants were cultivated under greenhouse conditions.

By analyzing total RNA in a Northern Blot analysis concerning the disappearance of the transcripts complementary to the cDNA, the success of the genetic modification of the plants was assessed. For this purpose, total RNA was isolated from leaves of transformed plants according to standard methods and subsequently separated electrophoretically on an agarose gel. Then it was transferred onto a nylon membrane and hybridized with a radioactively labelled probe having the sequence indicated under Seq ID No. 1 or a part thereof. In about 5–10% of the transformed plants the band indicating the specific transcript under Seq ID No. 1 was missing in the Northern Blot analysis. The plants were used for analyzing the starch quality.

EXAMPLE 7

The Construction of the Plasmid pB33-Anti-RL and the Introduction of the Plasmid into the Genome of Potato Plants By means of the restriction endonuclease Asp718, a DNA fragment with an approximate length of 1800 bp, which comprises a part of the open reading frame of the cDNA insertion was isolated from the plasmid pRL1 and was ligated into the vector B33-Hyg which was cut with Asp718. This vector was constructed as follows:

The 35S promoter was removed from the pBinAR Hyg vector (DSM 9505) by means of the restriction endonucleases EcoR I and Asp718. A fragment with a length of about 1526 bp comprising the B33 promoter was isolated from the plasmid p33-anti-BE (DSM 6146) by means of EcoR I and Asp718 and inserted into the pBinAR Hyg vector (DSM 9505) cut with EcoR I and Asp718.

By inserting the cDNA fragment into the Asp718 site of the B33-Hyg plasmid, an expression cassette is produced which consists of the fragments A, B and C as follows (FIG. 4):

Fragment A contains the B33 promoter from *Solanum tuberosum* (EP 3775 092; Rocha-Sosa et al., EMBO J. 8 (1989), 23–29).

Apart from flanking regions, fragment B contains a part of the protein encoding region of the cDNA insertion from the pRL1 plasmid. This was isolated as an Asp718 fragment from pRL1 as described above and fused to the B33 promoter in B33-Hyg in antisense orientation.

Fragment C (192 bp) contains the polyadenylation signal of gene 3 of the T-DNA of the Ti-plasmid pTiACH5 (Gielen et al., EMBO J. 3 (1984), 835–846).

The plasmid pB33-anti-RL has a size of approximately 12.8 kb.

The plasmid was transferred into potato plants by means of Agrobacteria-mediated transformation, as described above. From the transformed cells whole plants were regenerated. The transformed plants were cultivated under greenhouse conditions. By analyzing total RNA in a Northern Blot analysis concerning the disappearance of the transcripts complementary to the cDNA the success of the genetic modification of the plants was assessed. For this purpose, total RNA was isolated from tubers of transformed plants according to standard methods and subsequently separated electrophoretically on an agarose gel. Then it was transferred onto a nylon membrane and hybridized with a radioactively labelled probe showing the sequence indicated under Seq ID No. 1 or a part thereof. In about 5–10% of the transformed plants the band indicating the transcript hybridizing with the cDNA of the invention was missing in the Northern Blot Analysis. From these plants starch was isolated from tubers and analyzed as described in Example 8.

EXAMPLE 8

Analysis of the Transformed Potato Plants

The potato plants transformed according to Example 6 and Example 7 were examined with regard to the properties of the synthesized starch. Analyses were carried out with various lines of the potato plants which had been transformed with the plasmid p35S-anti-RL or the plasmid pB33-anti-RL and which in Northern Blot analysis had not exhibited the band indicating transcripts hybridizing to the DNA sequences of the invention.

a) Determination of the Viscosity of Aqueous Solutions of the Starch

In order to determine the viscosity of the aqueous solutions of the starch synthesized in transformed potato plants, starch was isolated from tubers of plants which had been transformed with the plasmid p35S-anti-RL or the plasmid pB33-anti-RL using standard methods. 30 g of starch were each taken up in 450 ml $H_2O$ and used for analysis in an E viscograph (Brabender OHG Duisburg (Germany)). The appliance was used according to the manufacturer's instructions. In order to determine the viscosity of the aqueous solution of the starch, the starch suspension was first heated from 50° C. to 96° C. at a speed of 3° C. per minute. The temperature was subsequently kept at 96° C. for 30 min. The solution was then cooled from 96° C. to 50° C. at a speed of 3° C. per minute. During the whole process the viscosity was determined. Representative results of such measurements are set forth in the form of graphs in FIGS. 3, 4 and 5, in which the viscosity is shown depending on time. FIG. 3 shows a typical Brabender graph for starch isolated from wildtype-plants of the potatoe variety Désirée. FIGS. 4 and 5 show a typical Brabender graph for starch isolated from potato plants which had been transformed with the plasmid p35S-anti-RL or pB33-anti-RL. From these graphs characteristic values may be deduced.

The characteristic values for wildtype-plants are as follows:

TABLE 1

| Value | Time [min:sec] | Torque [BE] | Temperature [° C.] |
|---|---|---|---|
| A | 6:30 | 60.5 ± 17.7 | 69.9 ± 0.57 |
| B | 11:30 | 1838.0 ± 161.2 | 86.0 ± 2.1 |
| C | 15:15 | 1412.0 ± 18.4 | 96.0 |
| D | 45:15 | 526.0 ± 17.0 | 96.0 |
| E | 60:30 | 812.0 ± 8.5 | 50.0 |
| F | 70:45 | 853.0 ± 5.7 | 50.0 |

The values represent the average values obtained from two different measurements.

In Table 1 and the following Tables 2 and 3 the abbreviations signify the following:

| | |
|---|---|
| A: | start of pastification |
| B: | maximum viscosity |
| C: | start of 96° C. period |
| D: | start of cooling-off time |
| E: | end of cooling-off time |
| F: | end of the end-50° C. period |

For plants which had been transformed with the plasmid p35S-anti-RL (line P2), the characteristic values are the following:

TABLE 2

| Value | Time [min:sec] | Torque [BE] | Temperature [° C.] |
|---|---|---|---|
| A | 6:00 | 50.0 | 69.0 |
| B | 14:00 | 820.0 | 93.0 |
| C | 15:15 | 815.0 | 96.0 |
| D | 45:15 | 680.0 | 96.0 |
| E | 60:30 | 1150.0 | 50.0 |
| F | 70:45 | 1200.0 | 50.0 |

For plants which had been transformed with the plasmid pB33-anti-RL (line P3), the characteristic values are the following:

TABLE 3

| Value | Time [min:sec] | Torque [BE] | Temperature [° C.] |
|---|---|---|---|
| A | 7:0 | 31.0 | 71.0 |
| B | 12:45 | 671.0 | 88.3 |
| C | 15:15 | 662.0 | 96.0 |
| D | 45:15 | 607.0 | 96.0 |
| E | 60:30 | 1063.0 | 50.0 |
| F | 70:45 | 1021.0 | 50.0 |

FIGS. 3, 4 and 5 explicitly show that the starch obtained from transformed plants differs from starch from wildtype plants particularly in that the viscosity increases only very slightly during heating. Thus, during heating the maximum viscosity of the modified starch from transformed plants is more than 50% lower than in the case of wildtype starch.

During cooling, on the other hand, the viscosity of the starch isolated from transformed plants increases more than in the case of wildtype-plants.

b) Determination of the Phosphate Content of the Starch

The phosphate content of the starch was determined by measuring the amount of phosphate bound to the C-6-position of the glucose residues. For this purpose, starch was first degraded by acid hydrolysis and the glucose-6-phosphate content was subsequently determined by means of an enzyme test, as described in the following.

100 mg starch were incubated in 500 µl 0.7 N HCl for 4 hours at 100° C. After acid hydrolysis 10 µl of the reaction were added to 600 µl imidazole buffer (100 mM imidazole, 5 mM $MgCl_2$, pH 6.9, 0.4 mM $NAD^+$). The amount of glucose-6-phosphate in the reaction mixture was determined by conversion with the enzyme glucose-6-phosphate-dehydrogenase. For this purpose, 1 U glucose-6-phosphate-dehydrogenase (from Leuconostoc mesenteroides (Boehringer Mannheim)) was added to the reaction mixture and the amount of produced NADH was determined by measuring the absorption at 340 nm.

The glucose-6-phosphate content of 1 mg starch is indicated in the following table for non-transformed potato plants of the variety Désirée as well as for two lines (P1 (35S-anti-RL); P2(35S-anti-RL)) of transgenic potato plants which had been transformed with the plasmid p35S-anti-RL.

TABLE 4

| Plants | nmol glucose-6-phosphate/mg starch | % |
|---|---|---|
| Wildtype | 12.89 ± 1.34 | 100 |
| P1 (35S-anti-RL) | 2.25 ± 0.41 | 17.4 |
| P2 (35S-anti-RL) | 1.25 ± 0 | 9.7 |

The following table shows the glucose-6-phosphate content per milligram starch in potato plants which were transformed with the plasmid pB33-anti-RL, compared to starch from non-transformed plants (S. tuberosum c.v. Désirée).

TABLE 5

| Plants | nmol glucose-6-phosphate/mg starch | % |
|---|---|---|
| Wildtype | 9.80 ± 0.68 | 100 |
| 7 | 4.50 ± 0.73 | 45.9 |
| 37 | 2.64 ± 0.99 | 26.9 |
| 45 | 1.14 ± 0.44 | 11.6 |
| 31 | 1.25 ± 0.49 | 12.8 |

The plants 7, 37, 45 and 31 represent independent transformants which had been transformed with the plasmid pB33- anti-RL. Plant 37 represents line P3 for which a Brabender graph is plotted in FIG. 5.

The values show that the phosphate content of the modified starch from transgenic potato plants is at least 50% lower when compared to starch from wildtype plants.

c) Determination of Glucose, Fructose and Sucrose Content of Tubers After Storage at 4° C.

Tubers of plants from various transgenic lines which had been transformed with the antisense-construct p35S-anti-RL as well as tubers of wildtype plants were stored at 4° C. or, respectively, at 20° C. in darkness, for two months. Subsequently, the amounts of glucose, fructose and sucrose were determined as described above. For two transgenic lines the representative values obtained were the following:

TABLE 6

|  | Glucose | | Fructose | | Sucrose | |
| --- | --- | --- | --- | --- | --- | --- |
|  | 20° C. | 4° C. | 20° C. | 4° C. | 20° C. | 4° C. |
| Wildtype cv Desiree | 0.84 | 55.4 | 0.62 | 52.8 | 8.5 | 13.1 |
| Transgenic line 15 | 1.12 | 6.7 | 0.75 | 7.8 | 7.5 | 10.1 |
| Transgenic line 11 | 1.00 | 6.4 | 0.75 | 7.5 | 6.9 | 6.9 |

The values in the table are indicated in μmol hexose or sucrose/g fresh weight.

From the values of Table 6 it becomes obvious that the accumulation of reducing sugars in the tubers is considerably lower in transgenic plants stored at 4° C. than in wildtype plants.

Altogether the modified starch isolated from transgenic potato plants resembles starch from maize-wildtype plants. However, in comparison it has the advantage that its taste is neutral and that it is therefore more suitable for various uses in the foodstuffs area.

EXAMPLE 9

Expression of the cDNA Insertion of the pRL2 Plasmid in E. Coli (a) Transformation of Bacterial Cells In order to express the cDNA insertion of the plasmid pRL2 the cells of the E.coli strain DH5α are first transformed with the pACAC plasmid. This plasmid contains a DNA fragment encoding the ADP-glucose-pyrophosphorylase (AGPase) from E.coli, under the control of the lac Z promoter. The fragment had been isolated from the vector pEcA-15 as a DraI/HaeII fragment with a size of about 1.7 kb (see B. Müller-Röber (1992), dissertation, FU Berlin) and after filling in its sticky ends it had been cloned into a pACAC184 vector linearized with HindIII. The expression of AGPase is to cause an increase of the glycogen synthesis in transformed E.coli cells. The cells transformed in such a way will in the following be named E.coli-K1-cells.

In order to determine the enzyme activity of the protein encoded by the cDNA of plasmid pRL2, E.coli-K1-cells were transformed with the pRL2 plasmid. The transformed E.coli cells which contain the pACAC plasmid as well as the pRL2 plasmid will in the following be named E.coli-K2-cells.

The transfer of the plasmid DNA into the bacterial cells was carried out according to the Hanahan method (J. Mol. Biol. 166 (1983), 557–580). The transformed E.coli cells were plated onto agar culture dishes with the following composition:

| YT medium containing | |
| --- | --- |
| 1.5% | Bacto agar |
| 50 mM | sodium phosphate buffer, pH 7.2 |
| 1% | glucose |
| 10 μg/ml | chloramphenicol in the case of E.coli-K1-cells or |
| 10 μg/ml | chloramphenicol and |
| 10 μg/ml | ampicillin in the case of E.coli-K2-cells. |

Escherichia coli cells of the DH5α strain which had been transformed with the plasmid pRL2+pACAC (E.coli-K2-cells) and also—for control—solely with the pACAC plasmid (E.coli-K1-cells), were raised on agar plates. The formed glycogen of the various cultures was examined with respect to the degree of phosphorylization (at the C-6 position of the glucose molecule), as described in the following.

(b) Isolation of Bacterial Glycogen

In order to isolate bacterial glycogen, the bacteria colony which had grown after transformation was floated from each 6 agar plates (Ø 135 mm) with 5 ml YT medium for each plate. The bacterial suspension was centrifuged at 4500×g for 5 minutes. The bacterial precipitate was resuspended in 10 ml YT medium. Disruption of the bacteria was carried out by adding 2 volumes of disruption medium (0.2 N NaOH; 1% SDS) and by incubation at room temperature for 5 minutes. By adding 3 volumes of EtOH abs., incubating at 4° C. for 30 minutes and subsequent centrifuging at 8000×g for 15 minutes, the glycogen was sedimented. Then the precipitate was washed with 100 ml of 70% EtOH and again sedimented by means of a centrifugation step (10 minutes at 8000×g). The washing procedure was repeated four times.

(c) Determination of the Total Glycogen Content

The isolated and sedimented glycogen was first degraded into single glucose molecules by means of acidic hydrolysis (dissolving of the precipitate in 2 ml 0.7 N HCl; incubation for 4 hours at 100° C.). The glucose content of the solution was determined by means of coupled enzymatic reaction of a starch test with a photometer (Kontron) at a wave length of 340 nm according to the manufacturer's (Boehringer Mannheim) instructions.

| The reaction buffer contains: | 100 mM MOPS, pH 7.5 |
| --- | --- |
| | 10 mM MgCl$_2$ |
| | 2 mM EDTA |
| | 0.25 mM NADP |
| | 1 mM ATP |
| | 1 U/ml glucose-6-phosphate-dehydrogenase |
| | 2 U/ml hexokinase |

Die measurement was carried out at 25° C. with 10 μl glucose solution.

(d) Determination of the Glucose-6-Phosphate Content

In order to determine the content of glucose molecules phosphorylated at the C-6 position, equal amounts of glucose of the various bacterial cultures were used. By adding the same volumes of 0.7 N KOH to the glycogens degraded into its glucose molecules by acidic hydrolysis (as above), the solution was neutralized.

| The reaction buffer contains: | 100 mM MOPS, pH 7.5 |
| --- | --- |
| | 10 mM MgCl$_2$ |
| | 2 mM EDTA |
| | 0.25 mM NADP |
| | 2 U/ml glucose-6-phosphate-dehydrogenase |

The measurement was carried out at 25° C. with 100 to 150 μl glucose solution.

(e) Identification of an Enzyme Activity Phosphorylating Bacterial Glycogen

The results of the determination of the phosphate content of the glycogen synthesized in the bacterial cells show that the glycogen of the *E.coli* cells, which had been transformed with the pACAC+pRL2 plasmids, exhibits a 290±25% increased phosphorylation at the C-6 position of the glucose when comparing with the control reaction (*E.coli* cells transformed with the pACYC plasmid) (see the following table).

| *E.coli* cells | glucose-6-phosphase:glucose in glycogen |
| --- | --- |
| *E.coli*-K1 | 1:(4600 ± 1150) |
| *E.coli*-K2 | 1:(1570 ± 390) |

The degrees of phosphorylation indicated herein are the average value of at least 6 measurements starting from 6 independent transformations and glycogen isolations.

EXAMPLE 10

Integration of the Plasmid p35S-Anti-RL in Combination with the Plasmid D35SH-Anti-BE into the Genome of Potato Plants The plasmid p35S-anti-RL was constructed as described in Example 6. The plasmid p35SH-anti-BE was constructed as described in the application WO95/07355, Example 3. Both plasmids were sequentially transferred into potato plants by means of the Agrobacterium mediated transformation as described above. For this purpose, the plasmid p35SH-anti-BE was first transformed in potato plants. Whole plants were regenerated and selected for a reduced expression of the branching enzyme gene. Subsequently, the plasmid p35S-anti-RL was transformed into the transgenic plants already showing a reduced expression of the branching enzyme. From the transformed cells transgenic plants were again regenerated and the transformed plants were cultivated under greenhouse conditions. By analyzing total RNA in an RNA Blot analysis with respect to the disappearance of the transcripts complementary to the branching enzyme cDNA or the RL cDNA, the success of the genetic modification of the plants with respect to a highly reduced expression of the branching enzyme gene as well as with respect to a highly reduced expression of the RL gene was assessed. For this purpose, total RNA was isolated from leaves of transformed plants according to the described methods and subsequently separated by means of gel electrophoresis, transferred onto a membrane, hybridized with a radioactively labelled probe showing the sequence indicated under Seq ID No. 1 or a part thereof and then hybridized with a radioactively labelled probe showing the sequence of the branching enzyme cDNA (cf. WO92/14827, Example 1) or a part thereof. In about 5%-10% of the transformed plants the band indicating the specific transcript of the sequence indicated under Seq ID No. 1 as well as the band indicating the specific transcript of the branching enzyme cDNA (cf. WO92/14827) was missing in the RNA Blot analysis. These plants, which were designated R4 plants were used for analyzing the quality of the starch contained in tubers.

EXAMPLE 11

Integration of the Plasmid pB33-Anti-RL in Combination with the Plasmid pB33-Anti-GBSSI into the Genome of Potato Plants The plasmid pB33-anti-RL was constructed as described in Example 7. The plasmid pB33-anti-GBSSI was constructed as follows:

The DraI/DraI fragment of the promoter region of the patatin class I gene B33 from *Solanum tuberosum* comprising the nucleotides −1512 to +14 (Rocha-Sosa et al., EMBO J 8 (1989), 23–29) was ligated into the SmaI site of the pUC19 plasmid. From the resulting plasmid the promoter fragment was ligated into the polylinker region of the pBin19 plasmid (Bevan, Nucleic Acids Research 12 (1984), 8711–8721) as an EcoRI/HindIII fragment. Subsequently, the 3' EcoRI fragment 1181 to 2511 of the GBSSI gene of *Solanum tuberosum* (Hergersberg, dissertation (1988), University of Cologne) was ligated into the EcoRI site of the resulting plasmid.

Both plasmids were transferred sequentially into potato plants by means of Agrobacterium mediated transformation as described in Example 10. From the transformed cells whole plants were regenerated and the transformed plants were cultivated under greenhouse conditions. By analyzing the complete RNA in a RNA Blot analysis with regard to the disappearance of the transcripts complementary to the two cDNAs, the success of the genetic modification of the plants was assessed. For this purpose, total RNA was isolated from tubers of transformed plants according to standard methods and subsequently separated on agarose gel by means of gel electrophoresis, transferred onto a membrane and hybridized with a radioactively labelled probe showing the sequence indicated under Seq ID No. 1 or a part thereof. Afterwards, the same membrane was hybridized with a radioactively labelled probe having the sequence of the GBSSI gene or a part of this sequence (Hergersberg, dissertation (1988) University of Cologne). In about 5%–10% of the transformed plants the band indicating the transcripts hybridizing to the cDNA of the invention or the GBSSI cDNA were missing in the RNA Blot analysis. From the tubers of these plants, which were designated R3 plants, starch was isolated and analyzed.

EXAMPLE 12

Starch Analysis of R4 Plants

The potato plants transformed according to Example 10 were examined with respect to the properties of the synthesized starch. The analyses were carried out with various lines of the potato plants which had been transformed with the plasmids p35S-anti-RL and p35SH-anti-BE and which did no longer—or only in extremely reduced form—show the bands indicating transcripts hybridizing to the DNA sequences of the invention or to the sequence of the branching cDNA in RNA Blot analysis.

a) Determination of the Viscosity of Aqueous Solutions of the Starch

In order to determine the viscosity of the aqueous solutions of the starch synthesized in transformed potato plants, starch was isolated from tubers of plants which had been transformed with the plasmid p35S-anti-RL and the plasmid p35SH-anti-BE using standard methods. 2 g of starch were each dissolved in 25 ml $H_2O$ and used for analysis with a Rapid Visco Analyser (Newport Scientific Pty Ltd, Investment Support Group, Warriewood NSW 2102, Australia). The equipment was used according to the instructions of the manufacturer. In order to determine the viscosity of the aqueous solution of the starch, the starch suspension was first heated from 50° C. to 95° C. with a speed of 12° C. per minute. The temperature was then kept at 95° C. for 2.5 minutes. Afterwards, the solution was cooled from 95° C. to 50° C. with a speed of 12° C. per minute. During the whole process the viscosity was measured. Representative results of such measurements are set forth in the form of graphs in which the viscosity is shown depending on time. FIG. 6 shows a typical RVA graph for starch isolated from the wildtype-plants of potato of the variety Désirée. Lines 2 and 3 show a typical RVA graph for starch isolated from the tubers of plants which had been transformed with the plasmid p35SH-anti-BE and with the plasmid p35S-anti-RL, respectively. Line 4 shows a typical RVA graph for starch isolated from tubers of plants which had been transformed with plasmid p35SH-anti-BE in combination with plasmid p35S-anti-RL. Line 4 is characterized in that there is no temperature-dependent increase of viscosity.

b) Determination of the Amylose/Amylopectin Ratio

Starch which was isolated from the tubers of transformed potato plants was examined with respect to the ratio of amylose to amylopectin. The plant line R4-1 (shown in line 4 of FIG. 6) exhibited an amylose content of more than 70%. For the plant line R4-3 an amylose value of 27% was measured, whereas the amylose content in wildtype starch of the Désirée variety ranges between 19 and 22%.

EXAMPLE 13

Starch Analysis of R3 Plants

The potato plants transformed according to Example 11 were examined with respect to the properties of the synthesized starch. The analyses were carried out with various lines of the potato plants which had been transformed with the plasmids pB33-anti-RL and pB33-anti-GBSSI and which did no longer—or only in extremely reduced form—show the bands indicating transcripts hybridizing to the DNA sequences of the invention or to the sequence of the GBSSI cDNA in RNA Blot analysis.

a) Determination of the Viscosity of Aqueous Solutions of the Starch

In order to determine the viscosity of the aqueous solution of the starch synthesized in transformed potato plants, starch was isolated from tubers of plants which had been transformed with the plasmid pB33-anti-RL in combination with the plasmid pB33-anti-GBSSI using standard methods. The viscosity was determined by means of a Rapid Visco Analyser according to the method described in Example 12, part a. The results are indicated in FIG. 7. In line 1, FIG. 7 shows a typical RVA graph for starch isolated from the wildtype-plants of the Désirée potato variety. Lines 2 and 3 show typical RVA graphs for starches isolated from potato plants which had been transformed with the plasmid pB33-anti-GBSSI and with the plasmid p35S-anti-RL, respectively. Line 4 shows a typical RVA graph for starch isolated from potato plants which had been transformed with the plasmid pB33-anti-GBSSI in combination with the plasmid pB33-anti-RL. This graph is characterized in that the maximum viscosity and the increase of viscosity at 50° C. are missing. Furthermore, this starch is characterized in that the glue obtained after RVA treatment exhibits almost no retrogradation after incubating at room temperature for several days.

b) Determination of the Amylose/Amylopectin Ratio

Starch which was isolated from the tubers of transformed potato plants was examined with respect to the ratio of amylose to amylopectin. The plant line R3–5 (shown in line 4 of FIG. 7) exhibited an amylose content of less than 4%. For the plant line R3–6 an amylose content of less than 3% was measured. The amylose content in wildtype starch of the Désirée variety ranges between 19 and 22%.

c) Determination of the Phosphate Content of Starch

The phosphate content of the starch was determined by measuring the amount of phosphate bound to the C-6-position of the glucose residues. For this purpose, starch was first degraded by acid hydrolysis and the glucose-6-phosphate content was subsequently determined by means of an enzyme test, as described in the following.

100 mg starch were incubated in 500 $\mu$l 0.7 N HCl for 4 hours at 100° C. After acid hydrolysis 10 $\mu$l of the reaction mixture were added to 600 $\mu$l imidazole buffer (100 mM imidazole, 5 mM $MgCl_2$, pH 6.9, 0.4 mM $NAD^+$). The amount of glucose-6-phosphate in the preparation is determined by conversion with the enzyme glucose-6-phosphate-dehydrogenase. For this purpose, 1 U glucose-6-phosphate-dehydrogenase (from Leuconostoc mesenteroides (Boehringer Mannheim)) was added to the reaction mixture and the amount of produced NADH was determined by measuring the absorption at 340 nm.

The glucose-6-phosphate content per 1 mg starch is indicated in the following table for non-transformed potato plants of the variety Désirée as well as for the R3-5 and the R3-6 line of transgenic potato plants which had been transformed with the plasmid pB33-anti-RL in combination with the plasmid pB33-anti-GBSSI. As a comparison, the value of the starch from the so-called waxy potato (US2-10) which had been transformed with the plasmid pB33-anti-GBSSI, is also indicated.

TABLE 7

| Plants | nmol glucose-6-phosphate/mg starch | % |
|---|---|---|
| Wildtype | 9.80 ± 0.68 | 100 |
| R3-5 | 1.32 ± 0.10 | 13 |
| R3-6 | 1.37 ± 0.15 | 14 |
| US2-10 | 10.82 ± 0.42 | 110 |

What is claimed is:

1. An isolated DNA molecule encoding an antisense-RNA complementary to a transcript of a nucleic acid molecule encoding a protein which is present in plant cells in starch granule-bound form as well as in soluble form and that is involved in the phosphorylation of starch when expressed in plants and/or that increases the phosphorylation of glycogen when expressed in E.coli, said nucleic acid molecule selected from the group consisting of:

(a) a nucleic acid molecule comprising a nucleotide sequence that encodes a protein having the amino acid sequence of SEQ ID NO: 2;
   (b) a nucleic avid molecule comprising the coding region of the nucleotide sequence of SEQ ID NO: 1;
   (c) a nucleic acid molecule that hybridizes to the nucleic acid molecule of (a) or (b) under stringent conditions wherein the nucleic acid molecule encodes a polypeptide that is present in plant cells in starch granule-bound form as well as soluble form and that is involved in the phosphorylation of starch when expressed in plants and/or that increases the phosphorylation of glycogen when expressed in E.coli;
   (d) a nucleic acid molecule the sequence of which is degenerate as a result of the genetic code to a nucleic acid molecule of (a), (b) or (c); and
   (e) a fragment or allelic variant of a nucleic acid molecule of (a), (b), (c), or (d), wherein the fragment or allelic variant encodes a polypeptide that is present in plant cells in starch granule-bound form as well as in soluble from and that is involved in the phosphorylation of starch when expressed in plants and/or that increases the phosphorylation of glycogen when expressed in E.coli, wherein said antisense-RNA is capable of inhibiting the expression of nucleic acid molecules encoding said protein when expressed in a plant cell.

2. A vector compromising the DNA molecule according to claim 1.

3. The vector of claim 2, wherein the DNA molecule is operably linked to regulatory elements ensuring transcription in a plant cell.

4. A host cell comprising the DNA molecule acording to claim 1 or comprising a vector comprising said DNA molecule.

5. A transgenic plant cell comprising the DNA molecule according to claim 1, wherein said DNA molecule is operably linked to regulatory elements ensuring transcription in a plant cell.

6. The transgenic plant cell of claim 5, in which the activity of at least one further enzyme involved in starch biosynthesis or modification is reduced when compared to non-transformed plants.

7. The transgenic plant cell of claim 6 in which the activity of a branching enzyme is reduced.

8. The transgenic plant cell of claim 6 in which the activity of a starch granule-bound starch synthase of the isotope I (GBSS I) is reduced.

9. An RNA molecule obtainable by transcription of the nucleic acid molecule according to claim 1.

10. A method for producing a tranagenic plant cell synthesizing a modified starch comprising the step of introducing the DNA molecule of claim 48 into the cell, thereby reducing in the cell the amount of a protein which is present in the plant cell in starch granule-bound form as well as in soluble form and that is involved in the phosphorylation of starch when expressed in plants and/or that increases the phosphorylatian of glycogen when expressed in E.coli, said protein encoded by a nucleic acid molecule selected from the group consisting of:

(a) a nucleic acid molecule encoding a protein with the amino-acid sequence inidicated in SEQ ID NO: 2;
   (b) a nucleic acid molecule comprising the coding region of the nucleotide sequence indicated in SEQ ID NO: 1;
   (c) a nucleic acid molecule hybridizing to a nucleic acid molecule of (a) or (b) under stringent conditions;
   (d) a nucleic acid molecule the sequence of which is degenerate as a result of the genetic code to a nucleic acid molecule of (a) or (b); and
   (e) a fragment, derivative or allelic variant of a nucleic acid molecule of (a), (b), (c) or (d), wherein the fragment, derivative or allelic variant encodes a polypeptide that is present in plant cells in starch granule-bound form as well as in soluble form and that is involved in the phospborylation of starch when expressed in plants and/or that increases tbe phosphorylation of glycogen when expressed in E.coli;

wherein said reduction of the amount of said protein is caused by an antisense effect and results in the plant cell producing a modified starch.

11. The method of claim 10, wherein the enzyme activity of at least one further enzyme involved in the starch biosynthesis and/or modification is reduced.

12. The method of claim 11 wherein the enzyme is a branching enzyme.

13. The method of claim 11 wherein the enzyme is a starch granule-bound starch synthase of the isotype I (GBSSI).

14. A plant cell obtainable by the method of claim 10.

15. A transgenic plant obtainable by regenerating the plant cell of claim 14.

16. A propagation material of the plant according to claim 15, wherein the propagation material comprises the plant cell.

17. The transgenic plant of claim 15 which is a potato plant.

18. A tuber of the potato plant of claim 17.

19. The tuber of claim 18 which in comparison to tubers of wild-type plants exhibits a reduced cold sweetening.

20. The transgenic plant cell of claim 5 wherein the amount of a protein is reduced in the transgenic plant cell when compared to the wild-type plant cell, wherein the protein is present in the plant cell in starch granule-bound form as well as in soluble form and that is involved in the phosphorylation of starch when expressed in plants and/or that increases the phosphorylation of glycogen when expressed in E.coli, and wherein the protein is encoded by a nucleic acid molecule selected from the group consisting of:

(a) a nucleic acid molecule encoding a protein with the amino-acid sequence indicated in SEQ ID NO: 2;

(b) a nucleic acid molecule comprising the coding region of the nucleotide sequence indicated in SEQ ID NO: 1;

(c) a nucleic acid molecule hybridizing to nucleic acid molecule of (a) or (b) under stringent conditions;

(d) a nucleic acid molecule the sequence of which is degenerate as a result of the genetic code to a nucleic acid molecule of (a) or (b), and (e) a fragment, derivative or audio variant of a nucleic acid molecule of (a), (b), (c), or (d), wherein the fragment, derivative or allelic variant encodes a polypeptide that is present in plant cells in starch granule-bound form as well as in soluble form and that is involved in the phosphorylation of starch when expressed in plants and/or that increases the phosphorylation of glycogen when expressed in E.coli.

21. A transgenic plant comprising the plant cell according to claim 5.

22. A transgenic plant comprising the plant cell according to claim 20.

23. The transgenic plant of claim 21 which is a potato plant.

24. The transgenic plant of claim 22 which is a potato plant.

25. A propagation material of the plant according to claim 21, wherein the propagation material comprises the plant cell.

26. A propagation material of the plant according to claim 22, wherein the propagation material comprises the plant cell.

27. A tuber of the potato plant of claim 23.

28. A tuber of the potato plant of claim 24.

29. The tranagenic plant of claim 15, wherein the plant is selected from the group consisting: of rye, barley, oats, wheat, rice, maize, peas and cassava.

30. The transgenic plant of claim 21, wherein the plant is selected from the group consisting of: rye, barley, oats, wheat, rice, maize, peas and cassava.

31. The transgenic plant of claim 22, wherein the plant is selected from the group consisting of: rye, barley, oats, wheat, rice, maize, peas and cassava.

32. The DNA molecule of claim 1, wherein the DNA molecule is more than 100 basepairs.

33. The DNA molecule of claim 32 wherein the DNA molecule is more than 500 basepairs.

34. An isolated DNA molecule encoding antisense-RNA complementary to a transcript of a nucleic acid molecule encoding a protein which is present in plant cells in starch granule-bound form as well as in soluble form and that is involved in the phosphorylation of starch when expressed in plants and/or that increases the phosphorylation of glycogen when expressed in E.coli, said nucleic acid molecule selected from the group consisting of:

(a) a nucleic acid molecule comprising a nucleotide sequence that encodes a protein having the amino acid sequence of SEQ ID NO: 2;

(b) a nucleic acid molecule comprising the coding region of the nucleotide sequence of SEQ ID NO: 1;

(c) a nucleic acid molecule that has more than 80% sequence identity to the nucleic acid molecule of (a) or (b);

(d) a nucleic acid molecule the sequence of which is degenerate as a result of the genetic code to a nucleic acid molecule of (a), (b) or (c); and (e) a fragment or allelic variant of a nucleic acid molecule of (a), (b), (c), or (d), wherein the fragment or allelic variant encodes a polypeptide that is present in plant cells in starch granule-bound form as well as in soluble form and that is involved in the phosphorylation of starch when expressed in plants and/or that increases the phosphorylation of glycogen when expressed in E.coli, wherein said antisense-RNA is capable of inhibiting the expression of nucleic acid molecules encoding said protein when expressed in a plant cell.

35. The DNA molecule of claim 34, wherein the nucleic acid molecule of (c) has more than 90% sequence identity to the nucleic acid molecule of (a) or (b).

36. The DNA molecule of claim 35, wherein the nucleic acid molecule of (c) has at least 95% complementarity to the nucleic acid molecule of (a) or (b).

* * * * *

UNITED STATES PATENT AND TRADEMARK OFFICE
CERTIFICATE OF CORRECTION

PATENT NO. : 6,815,581 B2
DATED : November 9, 2004
INVENTOR(S) : Jens Kossman and Ruth Lorberth It is certified that error appears in the above-identified patent and that said Letters Patent is hereby corrected as shown below:

Title page,
Item [56], References Cited, OTHER PUBLICATIONS, "Konecki et al." reference, change "Strucutre" to -- Structure --. "Napoli et al." reference, change "Resluts" to -- Results --.

Column 2,
Line 14, delete "of" after "starch".

Column 4,
Line 4, insert -- , -- after "conformation".
Line 14, insert -- , -- after "potato".

Column 5,
Line 8, change "this" to -- thus --.
Line 15, change "from" to -- form --

Column 6,
Line 44, insert -- , -- after "example".

Column 7,
Line 14, insert -- , -- after "cells".
Line 16, delete "," after "form".
Line 24, change "explicitely" to -- explicitly --.

Column 8,
Line 38, delete "the" before "dissolving".

Column 9,
Line 15, change "which" to -- with --.
Line 46, change "this" to -- these --.
Line 51, delete "the" before -- use --.
Line 64, change "vitamines" to -- vitamins --.

Column 10,
Line 52, change "potatoe" to -- potato --.
Line 61, insert -- , -- after "wheat".

Column 23,
Line 14, delete "-" between "restriction" and "endonucleases".
Line 14, change "potatoe" to -- potato --.

UNITED STATES PATENT AND TRADEMARK OFFICE
CERTIFICATE OF CORRECTION

PATENT NO. : 6,815,581 B2
DATED : November 9, 2004
INVENTOR(S) : Jens Kossman and Ruth Lorberth It is certified that error appears in the above-identified patent and that said Letters Patent is hereby corrected as shown below:

Column 57,
Line 40, change "avid" to -- acid --.
Line 43, insert -- , -- after "conditions".
Line 57, change "from" to -- form --.
Line 64, change "compromising" to -- comprising --.

Column 58,
Line 28, change "acording" to -- according --.
Line 43, change "isotope" to -- isotype --.
Line 46, change "tranagenic" to -- transgenic --.
Line 48, change "claim 48" to -- claim 1 --.
Line 53, change "phosphorylatian" to -- phosphorylation --.
Line 57, change "inidicated" to -- indicated --.

Column 59,
Line 4, change "phospborylatin" to -- phosphorylation --.
Line 5, change "tbe" to -- the --.
Line 19, change "obtainable by regenerating" to -- comprising --.
Line 44, insert -- a -- after "to".
Line 48, change "," to -- ; --.
Line 49, change "audio" to -- allelic --.

Column 60,
Line 11, change "tranagenic" to -- transgenic --.
Line 12, change "consisting: of" to -- consisting of: --.

Signed and Sealed this

Third Day of May, 2005

JON W. DUDAS
*Director of the United States Patent and Trademark Office*